(12) United States Patent
Ciurea et al.

(10) Patent No.: US 9,913,958 B2
(45) Date of Patent: Mar. 13, 2018

(54) PROTECTIVE SHEATHS FOR MEDICAL DEVICES

(71) Applicant: Abbott Cardiovascular Systems Inc., Santa Clara, CA (US)

(72) Inventors: Cornel I. Ciurea, Murrieta, CA (US); Karen J. Wang, Cupertino, CA (US); David Hart, Temecula, CA (US); Mark Ritchie, Fallbrook, CA (US); Jessie Madriaga, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 373 days.

(21) Appl. No.: 14/194,541

(22) Filed: Feb. 28, 2014

(65) Prior Publication Data
US 2015/0246203 A1    Sep. 3, 2015

(51) Int. Cl.
| | | |
|---|---|---|
| *B29C 65/00* | (2006.01) |
| *B29C 65/02* | (2006.01) |
| *B32B 37/00* | (2006.01) |
| *B32B 38/00* | (2006.01) |
| *B29D 22/00* | (2006.01) |

(Continued)

(52) U.S. Cl.
CPC ......... *A61M 25/0009* (2013.01); *B29C 57/04* (2013.01); *B29C 55/24* (2013.01); *B29C 66/5221* (2013.01); *B29C 66/71* (2013.01); *B29L 2031/7543* (2013.01)

(58) Field of Classification Search
CPC .......... A61F 2/95; A61F 2/958; A61F 2/9583; A61F 2/962; A61F 2/97; A61M 2025/1081; B29C 31/002; B29C 55/24; B29C 66/71; B29C 66/5221

USPC ... 156/60, 64, 196, 212, 213, 242, 245, 293, 156/294, 296, 349, 379, 391, 499, 500,
(Continued)

(56) References Cited

U.S. PATENT DOCUMENTS 3,776,682 A * 12/1973 Parmann ............... B29C 57/025
                                                        425/384
4,243,050 A    1/1981 Littleford
(Continued)

FOREIGN PATENT DOCUMENTS

EP          1 043 143        10/2000
WO        WO 98/00090         1/1998
(Continued)

OTHER PUBLICATIONS

"1/2 in. x 6 in. Flex Riser". The Home Depot. http://www.homedepot.com/p/1-2-in-x-6-in-Flex-Riser-37326/100373229.*
(Continued)

*Primary Examiner* — Philip Tucker
*Assistant Examiner* — Brian R Slawski
(74) *Attorney, Agent, or Firm* — Squire Patton Boggs (US) LLP

(57) ABSTRACT

A process for making a sheath used to protect a medical device. The medical device includes a polymer scaffold crimped to a catheter having an expansion balloon. A sheath is placed over the crimped scaffold after crimping to reduce recoil of the crimped polymer scaffold and maintain scaffold-balloon engagement relied on to hold the scaffold to the balloon when the scaffold is being delivered to a target in a body. The sheath is removed by a health professional either by removing the sheath directly or using a tube containing the catheter.

19 Claims, 11 Drawing Sheets

(51) Int. Cl.
  *A61F 2/06* (2013.01)
  *A01J 21/00* (2006.01)
  *A01J 25/12* (2006.01)
  *A21C 3/00* (2006.01)
  *A21C 11/00* (2006.01)
  *B28B 11/00* (2006.01)
  *B28B 21/00* (2006.01)
  *A61M 25/00* (2006.01)
  *B29C 57/04* (2006.01)
  *B29C 55/24* (2006.01)
  *B29L 31/00* (2006.01)

(58) Field of Classification Search
  USPC ....... 156/538, 539; 623/1.11, 1.12; 264/167, 264/292, 322; 425/393
  See application file for complete search history.

(56) References Cited

U.S. PATENT DOCUMENTS

| | | | |
|---|---|---|---|
| 4,276,010 A * | 6/1981 | Shartzer | B29B 13/025 425/143 |
| 4,449,904 A * | 5/1984 | Austen | B29C 47/0004 264/320 |
| 4,545,951 A * | 10/1985 | Gordon | B29C 57/08 264/322 |
| 4,581,025 A | 4/1986 | Sheath | |
| 4,710,181 A | 12/1987 | Fuqua | |
| 4,826,028 A * | 5/1989 | Vassallo | B29C 57/025 277/615 |
| 5,015,231 A | 5/1991 | Keith et al. | |
| 5,158,545 A | 10/1992 | Trudell et al. | |
| 5,211,654 A | 5/1993 | Kaltenbach | |
| 5,250,033 A | 10/1993 | Evans et al. | |
| 5,352,236 A | 10/1994 | Jung et al. | |
| 5,458,615 A | 10/1995 | Klemm et al. | |
| 5,527,503 A * | 6/1996 | Rowley | B29C 57/04 264/296 |
| 5,545,211 A | 8/1996 | An et al. | |
| 5,569,294 A | 10/1996 | Parkola | |
| 5,591,226 A | 1/1997 | Trerotola et al. | |
| 5,647,857 A | 7/1997 | Anderson et al. | |
| 5,653,697 A | 8/1997 | Quiachon et al. | |
| 5,693,066 A | 12/1997 | Rupp et al. | |
| 5,709,703 A | 1/1998 | Lukic et al. | |
| 5,749,852 A | 5/1998 | Schwab et al. | |
| 5,765,682 A | 6/1998 | Bley et al. | |
| 5,776,141 A | 7/1998 | Klein et al. | |
| 5,782,855 A | 7/1998 | Lau et al. | |
| 5,817,100 A | 10/1998 | Igaki | |
| 5,868,707 A | 2/1999 | Williams et al. | |
| 5,893,868 A | 4/1999 | Holman et al. | |
| 5,964,730 A | 10/1999 | Williams et al. | |
| 6,010,529 A | 1/2000 | Herweck et al. | |
| 6,110,146 A | 8/2000 | Berthiaume et al. | |
| 6,132,450 A | 10/2000 | Hanson et al. | |
| 6,146,572 A * | 11/2000 | Visscher | B29B 13/024 264/230 |
| 6,152,944 A | 11/2000 | Holman et al. | |
| 6,197,016 B1 | 3/2001 | Fourkas et al. | |
| 6,254,609 B1 | 7/2001 | Vrba et al. | |
| 6,334,867 B1 | 1/2002 | Anson | |
| 6,342,066 B1 | 1/2002 | Toro et al. | |
| 6,355,013 B1 | 3/2002 | Van Muiden | |
| 6,416,529 B1 | 7/2002 | Holman et al. | |
| 6,447,540 B1 | 9/2002 | Fontaine et al. | |
| 6,487,889 B1 * | 12/2002 | Bates | B21D 7/063 72/459 |
| 6,533,806 B1 | 3/2003 | Sullivan et al. | |
| 6,749,584 B2 | 6/2004 | Briggs et al. | |
| 6,783,542 B2 | 8/2004 | Eidenschink | |
| 6,790,224 B2 | 9/2004 | Gerberding | |
| 6,805,703 B2 | 10/2004 | McMorrow | |
| 6,827,731 B2 | 12/2004 | Armstrong et al. | |
| 6,899,727 B2 | 5/2005 | Armstrong et al. | |
| 7,198,636 B2 | 4/2007 | Cully et al. | |
| 7,314,481 B2 | 1/2008 | Karpiel | |
| 7,347,868 B2 | 3/2008 | Burnett et al. | |
| 7,384,426 B2 | 6/2008 | Wallace et al. | |
| 7,618,398 B2 | 11/2009 | Holman et al. | |
| 7,998,404 B2 | 8/2011 | Huang et al. | |
| 8,414,528 B2 | 4/2013 | Liu et al. | |
| 8,539,663 B2 | 9/2013 | Wang et al. | |
| 8,539,993 B2 | 9/2013 | Hagano | |
| 8,752,265 B2 | 6/2014 | Wang | |
| 2001/0001128 A1 | 5/2001 | Holman et al. | |
| 2002/0052640 A1 | 5/2002 | Bigus et al. | |
| 2002/0099431 A1 | 7/2002 | Armstrong et al. | |
| 2003/0004561 A1 | 1/2003 | Bigus et al. | |
| 2003/0212373 A1 | 11/2003 | Hall et al. | |
| 2004/0073286 A1 | 4/2004 | Armstrong et al. | |
| 2004/0143315 A1 | 7/2004 | Bruun et al. | |
| 2006/0015171 A1 | 1/2006 | Armstrong et al. | |
| 2006/0178739 A1 * | 8/2006 | Shalaby | A61F 2/90 623/1.49 |
| 2008/0010947 A1 | 1/2008 | Huang et al. | |
| 2009/0221965 A1 | 9/2009 | Osypka | |
| 2010/0004735 A1 | 1/2010 | Yang et al. | |
| 2011/0184509 A1 | 7/2011 | Von Oepen et al. | |
| 2012/0042501 A1 | 2/2012 | Wang et al. | |
| 2012/0109281 A1 | 5/2012 | Papp | |
| 2012/0261858 A1 | 10/2012 | Roberts et al. | |
| 2012/0285609 A1 | 11/2012 | Wang | |
| 2012/0324696 A1 | 12/2012 | Liu et al. | |
| 2013/0067907 A1 * | 3/2013 | Greene | C22F 1/10 60/527 |
| 2013/0253466 A1 * | 9/2013 | Campbell | A61M 25/10 604/500 |
| 2013/0305512 A1 * | 11/2013 | Green | A61F 2/86 29/428 |
| 2013/0327113 A1 * | 12/2013 | Green | B21D 39/20 72/342.7 |
| 2013/0327450 A1 * | 12/2013 | Green | A61F 2/82 148/563 |
| 2014/0096357 A1 | 4/2014 | Wang | |
| 2014/0157567 A1 | 6/2014 | Wang | |
| 2014/0208820 A1 * | 7/2014 | Houle | B21D 7/063 72/369 |
| 2014/0379064 A1 | 12/2014 | Pacetti et al. | |

FOREIGN PATENT DOCUMENTS

| | | |
|---|---|---|
| WO | WO 98/39056 | 9/1998 |
| WO | WO 02/060345 | 8/2002 |
| WO | WO 2011/094048 | 8/2011 |
| WO | WO 2013/184184 | 12/2013 |

OTHER PUBLICATIONS

"1-1/8 in. O.D. × 6-1/2 in. L Tub Rim Mount Risers in Polished Brass". The Home Depot. http://www.homedepot.com/p/Elizabethan-Classics-1-1-8-in-O-D-x-6-1-2-in-L-Tub-Rim-Mount-Risers-in-Oil-Rubbed-Bronze-EC2RMSWAC-ORB/202920024.*
International Search Report for PCT/US2015/018042, dated May 29, 2015, 10 pgs.
U.S. Appl. No. 13/644,347, filed Oct. 4, 2012, Wang.
U.S. Appl. No. 13/708,638, filed Dec. 7, 2012, Wang et al.
U.S. Appl. No. 13/840,257, filed Mar. 15, 2013, Hossainy et al.
U.S. Appl. No. 13/924,421, filed Jun. 21, 2013, Pacetti et al.

* cited by examiner

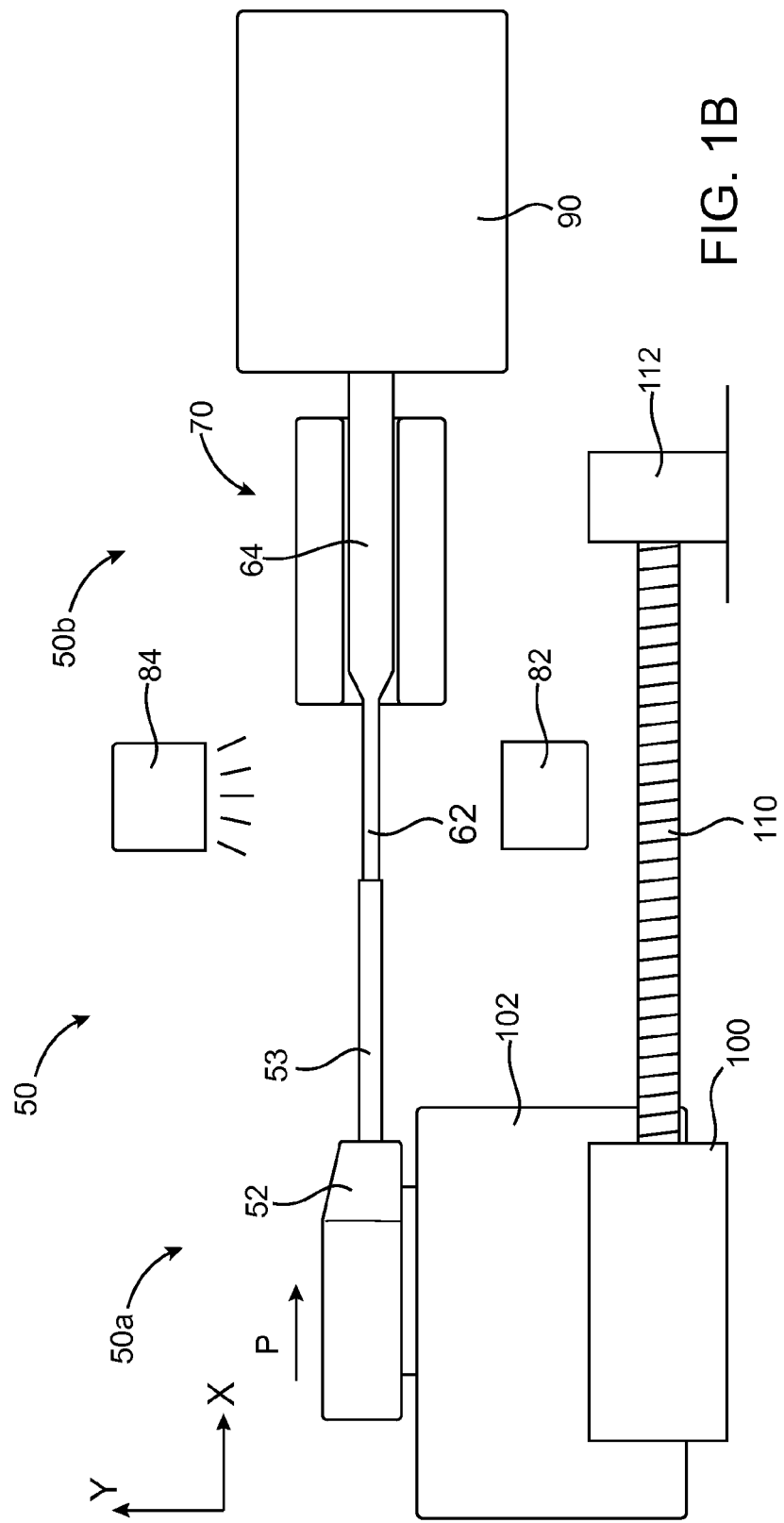

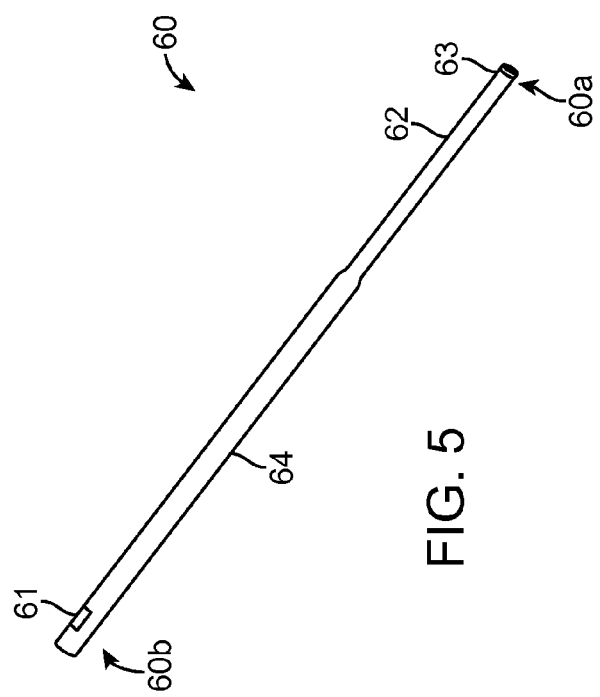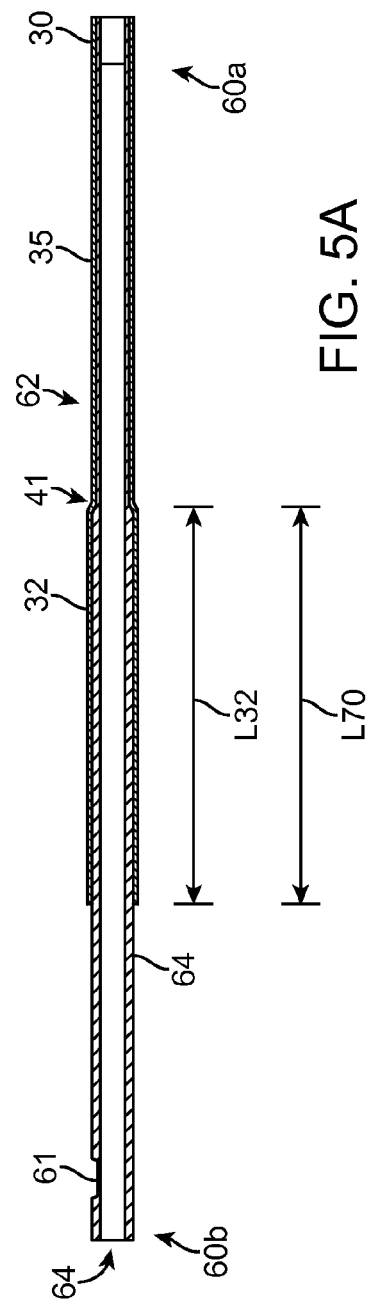

PROTECTIVE SHEATHS FOR MEDICAL DEVICES

FIELD OF THE INVENTION

The present invention relates to drug-eluting medical devices; more particularly, the invention relates to protective sheaths for scaffolds and stents crimped to a delivery balloon.

BACKGROUND OF THE INVENTION

A variety of non-surgical interventional procedures have been developed over the years for opening stenosed or occluded blood vessels in a patient caused by the build up of plaque or other substances in the walls of the blood vessel. Such procedures usually involve the percutaneous introduction of an interventional device into the lumen of the artery. In one procedure the stenosis can be treated by placing an expandable interventional device such as an expandable stent into the stenosed region to expand and hold open the segment of blood vessel or other arterial lumen. Metal or metal alloy stents have been found useful in the treatment or repair of blood vessels after a stenosis has been compressed by percutaneous transluminal coronary angioplasty (PTCA), percutaneous transluminal angioplasty (PTA) or removal by other means. Metal stents are typically delivered in a compressed condition to the target site, then deployed at the target into an expanded condition or deployed state to support the vessel.

The following terminology is used. When reference is made to a "stent", this term will refer to a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure. The disclosure herein applies to both stents and scaffolds.

Scaffolds and stents traditionally fall into two general categories—balloon expanded and self-expanding. The later type expands to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. However, self-expanding stents do not undergo, or undergo relatively no plastic or inelastic deformation when stowed in a sheath or placed on a balloon. Balloon expanded stents or scaffolds, by contrast, undergo a significant plastic or inelastic deformation when both crimped and later deployed by a balloon.

Self-expanding stents use sheaths to maintain a low profile and retain the stent on a delivery catheter. Once at the target site, the sheath is then removed or withdrawn in a controlled manner to facilitate deployment or placement at the desired site. Examples of self-expanding stents constrained within a sheath when delivered to a target site within a body are found in U.S. Pat. No. 6,254,609, US 20030004561 and US 20020052640. Balloon expanded stents may also be stored within a sheath, either during a transluminal delivery to a target site or during the assembly or in the packaging of the stent-balloon catheter delivery system. The balloon expanded stent may be contained within a sheath when delivered to a target site to minimize dislodgment of the stent from the balloon while en route to the target vessel. Sheaths may also be used to protect a drug eluting stent during a crimping process, which presses or crimps the stent to the balloon catheter. When an iris-type crimping mechanism, for example, is used to crimp a stent to balloon, the blades of the crimper, often hardened metal, can form gouges in a drug-polymer coating or even strip off coating through interaction similar to forces at play when the blades and/or stent struts are misaligned during the diameter reduction. Examples of stents that utilize a sheath to protect the stent during a crimping process are found in U.S. Pat. No. 6,783,542 and U.S. Pat. No. 6,805,703.

A polymer scaffold, such as that described in US 20100004735 may be made from a biodegradable, bioabsorbable, bioresorbable, or bioerodible polymer. The terms biodegradable, bioabsorbable, bioresorbable, biosoluble or bioerodible refer to the property of a material or stent to degrade, absorb, resorb, or erode away after the scaffold has been implanted at the target vessel. Polymer scaffolds described in US 2010/0004735 and US20110190872, as opposed to a metal stent, are intended to remain in the body for only a limited period of time. In many treatment applications, the presence of a stent in a body may be necessary for a limited period of time until its intended function of, for example, maintaining vascular patency and/or drug delivery is accomplished. Polymeric materials considered for use as a polymeric scaffold include poly(L-lactide) ("PLLA"), poly (L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex.

When using a polymer scaffold, several of the accepted processes for metal stent handling can no longer be used. A metal stent may be crimped to a balloon in such a manner as to minimize, if not eliminate recoil in the metal structure after removal from the crimp head. Metal materials used for stents are generally capable of being worked more during the crimping process than polymer materials. This desirable property of the metal can mean less concern over the metal stent—balloon engagement changing over time when the stent-catheter is packaged and awaiting use in a medical procedure. Due to the material's ability to be worked during the crimping process, e.g., successively crimped and released at high temperatures within the crimp mechanism, any propensity for elastic recoil in the material following crimping can be significantly reduced, if not eliminated, without affecting the stent's radial strength when later expanded by the balloon. As such, following a crimping process the stent-catheter assembly often does not need packaging or treatment to maintain the desired stent-balloon engagement and delivery profile. If the stent were to recoil to a larger diameter, meaning elastically expand to a larger diameter after the crimping forces are withdrawn, then significant dislodgment force could be lost and the stent-balloon profile not maintained at the desired diameter needed to deliver the stent to the target site. Consequently, sheaths for metallic stents are often solely protective, preventing contamination or mechanical damage to the stent and coating. They do not need to be closely fitted to prevent stent recoil on aging and storage.

While a polymer scaffold may be formed so that it is capable of being crimped in such a manner as to reduce inherent elastic recoil tendencies in the material when crimped, e.g., by maintaining crimping blades on the scaffold surface for an appreciable dwell period, the effectiveness of these methods are limited. Significantly, relatively high stiffness and brittle polymer material is generally incapable of being worked to the degree that a metal stent may be worked without introducing deployed strength problems, such as excessive cracking in the material.

U.S. Pat. No. 8,414,528 proposes a two-piece sheath intended for removal by a medical professional at the time of the medical procedure. The sheaths are placed over the crimped polymer scaffold shortly after crimping, for purposes of reducing or limiting the amount of recoil up until the time of use. The sheaths are designed to apply a radial constraint for limiting recoil while, at the same time, allowing a medical professional to easily remove the sheath without damaging the catheter or scaffold.

There is a need to improve upon sheaths used to protect medical devices either during processing, manufacture or, in the case of U.S. Pat. No. 8,414,528, to protect the medical device while it awaits use and/or to facilitate easy removal by a medical professional. There is also a need for improving upon the methods or processes for making such sheaths.

SUMMARY OF THE INVENTION

The invention is directed to sheaths and/or sheath assemblies used to maintain a polymer scaffold balloon engagement and delivery system profile and methods of manufacture of such sheaths.

According to one aspect, a sheath used to protect a scaffold is made from a hollow, polymer tube having a nominal diameter. The tube is reformed to have an enlarged, increased or widened diameter. This widened portion of the sheath has, in some embodiments, a length equal to about one half of the entire length of the sheath or at least about the entire length of the scaffold. The remaining portion of the re-formed tube has the nominal tube diameter. Between the nominal and widened diameter there is a sloped transition, such that the sheath steps up to the widened diameter at the transition. An example of this sheath is shown in FIG. 8A.

The inventors found that the manufacture of a sheath having a widened portion (larger diameter) and nominal portion (starting tube diameter) proved to be challenging. Several attempts were made to manufacture the sheath. For example, a sheath was made having the two diameters by attaching different diameter tubes to each other. An example of such a construction is illustrated in FIG. 7D of U.S. application Ser. No. 13/924,421 filed Jun. 21, 2013. It was found that the separate tubes used to make the sheath in this manner were capable of separating from each other. An acceptable solution, producing a robust and reliable sheath, as well has being expandable to commercial production for medical devices, was found in the following process:

1. Load tubing;
2. a mandrel for flaring the tube is heated at the widened portion (the mandrel has a narrow portion—small diameter—for receiving the tube and a widened portion—large diameter);
3. insert mandrel narrow portion into tube;
4. with mandrel wide portion heated push tube over wide portion;
5. heat set tube over wide portion; and
6. cool sheath over heat set portion.

In a preferred embodiment an apparatus for making a plurality of sheaths according to the above steps is provided. The apparatus includes a heating nozzle and mandrels that can produce three sheaths simultaneously. A partially open heating space within the nozzle can produce consistent/even heating across all three mandrels. The nozzle makes possible an easily implemented (i.e., few moving parts and process controls) automated process for making several sheaths at the same time. The preferred embodiment also uses hollow mandrels, which facilitates a more rapid heating and cooling time for sheaths formed on the mandrels.

An example of a sheath made according to the disclosure is shown in FIG. 7A. A sheath of this type may be used to protect a medical device, such as scaffold or stent, during assembly, production or handling, e.g., protect a coating or to limit recoil, or it may be used to protect a finished goods catheter as in the preferred embodiment. A sheath having the different diameters as illustrated in FIG. 7A may form a sheath portion for a sheath used to protect a scaffold as in portion 50 illustrated FIGS. 5 and 6A of US2012/0324696 having the two sections 32 and 35 in FIG. 7A.

In some embodiments a sheath made according to the above process is used with a second sheath to protect a scaffold. The sheath made according to the above process provides a constraining force on the scaffold (constraining sheath) while the second sheath, which is received within the constraining sheath, is placed between the constraining sheath and scaffold surface to act as a protecting sheath. The protecting sheath has stepped ends and the tube is cut into two halves. The assembly of the two sheaths may proceed in the following order.

A proximal end of the protecting sheath is flared and the tube cut about half way to make separable halves;
the protecting sheath is placed within the constraining sheath; and
while within the constraining sheath the distal end of the protecting sheath is flared or stepped.

Thereafter the stepped ends retain the constraining sheath on the protecting sheath, which facilitates removal of both sheaths with a distal pulling of the constraining sheath by a medical professional.

Sheaths made according to the above process are particularly useful for maintaining scaffold-balloon engagement and desired delivery profile following a crimping process where the scaffold is crimped down to achieve a smaller crossing-profile. A scaffold formed at a larger diameter, near to or greater than the expanded or post-dilation diameter, can exhibit enhanced radial strength when supporting a vessel, as compared to a scaffold formed nearer to a crimped diameter. A scaffold formed near to an expanded or post-dilation diameter, however, increases the propensity for elastic recoil in the scaffold following the crimping process, due to the shape memory in the material. The shape memory relied on for enhancing radial strength at deployment, therefore, also introduces greater elastic recoil tendencies for the crimped scaffold. Recoil both increases the crossing profile and reduces the scaffold-balloon engagement needed to hold the scaffold on the balloon. In one aspect, the invention is directed to maintaining the crossing profile and/or maintaining balloon-scaffold engagement for scaffolds formed near to a deployed diameter.

In another aspect, the invention is directed to a method of assembly of a catheter that includes crimping a polymer scaffold to a balloon of the catheter and within a short period of removal of the scaffold from the crimper placing a restraining sheath over the scaffold. The steps may further include applying an extended dwell time following a final crimping of the scaffold, followed by applying the restraining sheath. Both the crimping dwell time and applied restraining sheath are intended to reduce recoil in the crimped scaffold. The restraining sheath may include both a protecting sheath and a constraining sheath.

In another aspect, the invention is directed to a sterilized medical device, e.g., by E-beam radiation, contained within a sterile package, the package containing a scaffold crimped to a balloon catheter and a sheath disposed over the crimped scaffold to minimize recoil of the crimped scaffold. The sheath covers the crimped scaffold and may extend beyond the distal end of the catheter to facilitate removal from the scaffold. The sheath may extend at least the length of the scaffold beyond the distal end of the catheter. At the distal end of the sheath there is a portion configured for being manually grabbed and pulled distally of the catheter to remove the sheath from the catheter.

In another aspect, the invention is directed to an apparatus and methods for removing a sheath pair from a scaffold in a safe, intuitive manner by a health professional. According to this aspect of the invention, the sheath pair may be removed by a medical specialist such as a doctor without risk of the scaffold becoming dislodged from the balloon or damaged, such as when the sheath pair is accidentally removed in an improper manner by a health professional.

In accordance with the foregoing disclosure and within the scope of the invention is a scaffold and/or sheath(s), medical device, method for making and/or assembling such a scaffold and/or sheath, a system, method or apparatus for forming one or more sheaths from one or more blanks, or method for making and/or assembly of a medical device (such as a scaffold-balloon catheter assembly) comprising such a scaffold and/or sheath having one or more, or any combination of the following things (1)-(34):

(1) A nozzle for forming a sheath.
(2) A hollow mandrel for forming a sheath.
(3) The hollow mandrel is thin-walled. The mandrel may have a maximum ratio of outer diameter to wall thickness of between about 15 and 5, or more preferably between 11 and 8.
(4) A heating nozzle having a heating space with three openings with dimensions of W70, height H70 and length L70 allowing passage of one or a plurality of mandrels into the nozzle (in a first direction) and out of the nozzle (in a second direction).
(5) A sheath having two cylindrical portions of different diameter and made from a unitary piece of tubing. The cylindrical portions are joined by a sloped section, or a frusto-conical portion of the sheath.
(6) A two-piece sheath assembly.
(7) An apparatus for making one sheath or a plurality of sheaths, e.g., three sheaths, simultaneously.
(8) An apparatus for flaring a sheath over a mandrel. The apparatus may be configured to flare the sheath when a control signal indicates the sheath is properly loaded on the mandrel or a control system prevents the flaring of the sheath over the mandrel if the control system detects that the sheath was improperly loaded on the mandrel.
(9) A flow process for forming a sheath including one or any combination of loading a tube or sheath blank on a mandrel, forming the sheath with heat, and cooling the sheath over the mandrel.
(10) A detection system for detecting whether a blank is loaded properly upon a mandrel before a forming process begins, including a computer having stored on a non-transitory medium executable instructions for preventing, allowing or initiating the start of a sheath forming process; a means for detecting a sheath and/or mandrel, a light emitter and a light receiver, or an area sensor ("sensor") that emits a signal; a mandrel and the blank disposed within a detection area, e.g., mandrel 60 and tube 53 between portions 82 and 84. Wherein the instructions, when executed on the computer receive the signal and based on the value of the signal, the computer prevents, allows or initiates the forming process based on whether a blank dimension is detected within or outside of a range of approximately +\−20% (range to accommodate for variation in blank dimensions, such as an outer diameter). When the sensor has an output within this range the process begins. Below this range indicates the blank is not installed over the mandrel and the forming process does not begin. Above this range indicates the blank is present but missaligned or not properly installed with respect to the mandrel and the process does not begin. The signal may be a varying analog output signal based upon the percent of the beam being block, the beam being emitted from an emitter and received by a receiver. The computer, upon receiving the signal makes a determination on whether to initiate or allow proceeding or preventing the forming process from beginning/initiating.

(11) A two piece sheath assembly disposed over a scaffold.
(12) Referring to FIGS. 7A-7C a sheath having a length L30=L32+L35. The length L30 may be about or slightly less than L20. L20 may be longer than L30 by an amount about equal to the length of raised end 22. The inner diameter of portion L35 is less than the outer diameter of end 22 so that end 22 acts as a stop for sheath 30 when sheath 30 is pulled distally during removal from the catheter. L32 is greater than or about equal to the length of the balloon/scaffold.
(13) The lengths L32 and/or L35 may be based on a length of a scaffold. For example, both L32 and L35 may be about or at least the length of a scaffold, so that the L30 is about twice the length of the scaffold. Scaffold lengths for coronary use may be about 12 mm, 18 mm, 20 mm or 30 mm. The lengths L32 and/or L35 may therefore be about or at least 12 mm, 18 mm, 20 mm or 30 mm or be about or at least 12-20 mm, or be about or at least 12-18 mm or be about or at least 20-30 mm. Scaffold lengths for peripheral use may be about 30 mm, 40 mm, 50 mm, 60 mm, 100 mm, or 200 mm. The lengths L32 and/or L35 may therefore be about or at least 30 mm, 40 mm, 50 mm, 60 mm, 100 mm, or 200 mm or be about or at least 30-60 mm, or be about or at least 100 to 200 mm or be about or at least 60-150 mm.
(14) Before the sheaths are placed, the scaffold is crimped to the balloon using a crimping mechanism. For a polymer scaffold the diameter reduction during crimping may be 2:1, 2.5:1, 3:1, 4:1 or higher. The scaffold may be placed on a balloon having a nominal, expanded or post-dilation diameter that is about 2, 2.5, or 3 times the diameter of the scaffold when the scaffold has a final crimp diameter on the balloon.
(15) A sheath made according to the following steps: load tubing into a hand-held mold or a sheath holder; heat mandrel having a narrow end (small diameter) for receiving tube and widened portion (large diameter) for flaring; insert mandrel narrow portion into tube; with mandrel wide portion heated push tube over wide portion; heat set tube over wide portion; and cool sheath over mandrel.
(16) The sheath removal process described in FIGS. 8A-8C.
(17) A crimping process at or near to a glass transition temperature of the polymer of the scaffold conducted in the manner explained in U.S. application Ser. No. 13/644,347 including FIGS. 3A and 4A.

(18) Ratio of crimped diameter to balloon nominal inflation diameter or expanded diameter is greater than about 2, 2.5 or greater than about 3 or 4; and/or the ratio of pre-crimp diameter to balloon nominal diameter is about 0.9 to 1.5.

(19) The catheter and scaffold are configured as a medical device suitable for being implanted within a body only after a sheath(s) is/are removed. The catheter is not configured or suitable for implantation when the sheath pair is over the scaffold; or is implanted in use only after the sheath pair are removed by pulling the sheath pair distally form the catheter to remove the sheath pair from the catheter. The pulling may include gripping an outer or constraining sheath and pulling it distally (while the catheter is held stationary) so as to cause removal of both the outer or constraining sheath and inner or protecting sheath.

(20) A sheath, when protecting a crimped scaffold, has a constraining sheath covering at least the entire length of the scaffold and balloon and may extend beyond a distal tip of the catheter by at least a scaffold length, ½ a scaffold length or ¼ of a scaffold length, and/or the distal end of a protecting sheath.

(21) A protecting sheath has one or two flared, stepped or notched ends, or no stepped or notched ends.

(22) A constraining sheath length that is less, about equal to, or greater than a protecting sheath length.

(23) A method for making a sheath includes placing a protecting sheath within a constraining sheath, and then raising the ends of the protecting sheath when the protecting sheath is within the constraining sheath, where the raised ends resist removal of the constraining sheath from the protecting sheath.

(24) The protecting and/or constraining sheath may comprise PTFE, PVDF, fluoropolymer, polyethylene, polypropylene, nylon, nylon copolymers, Pebax, polyacetal, or polyimide.

(25) The polymer comprising the scaffold is bioresorbable, or the stent comprises a durable, non-bioresorbable, or non-bioerodible polymer.

(26) A constraining sheath has at least a first and second portion distinguished by their outer diameters—a first outer diameter corresponding to the first sheath portion that can apply a radial constraining force on the scaffold, and a second outer diameter, greater than the first outer diameter, corresponding to the second sheath portion that is located distal and/or proximal of the first sheath portion when the first sheath portion is disposed over the scaffold.

(27) A method for maintaining a low crossing profile and/or retention for a polymer includes crimping a scaffold to a balloon, placing a first sheath over the crimped scaffold; and replacing the first sheath with a second sheath.

(28) A system, comprising a heating space; a tube having a length and forming a cylindrical portion having a first diameter, the cylindrical portion extending over at least 25% of the length; a mandrel having a varying diameter over its length and being at least partially disposed within the heating space; and a tube holder holding the tube; wherein the tube holder pushes the tube over the mandrel to thereby form a shaped tube having the cylindrical portion first diameter increased to a second diameter.

(29) The system of (28), method of (30), apparatus of (32), (33) or (34), in combination with one of, more than one of, or any combination in any order of the following list of things: wherein the mandrel is a hollow mandrel; wherein the mandrel has only a small and large diameter section and a sloped section separating the diameter sections; wherein the large section is cylindrical and has the second diameter; wherein the large section has a length greater than the length of the cylindrical portion; wherein the entire large diameter section is disposed within the heating space and none of the small diameter section is disposed within the heating space; further comprising a heating nozzle, the nozzle comprising an upper and lower housing and an opening including the heating space between the housings; and/or wherein the openings permit passage of the mandrel into the heating space in a first direction and removal of the mandrel from the heating space in a second direction that is about perpendicular to the first space; wherein a plurality of the mandrels are disposed within the heating space; wherein the heating space is connected to a heat source supplying a gas having a temperature of at least 500 Deg. F; wherein the temperature throughout the heating space varies by 1-5% or less than 1% from the supply gas temperature; wherein the tube size is less than 80 mm and the tube length is between 20 and 200 mm; wherein the tube holder is coupled to a motor configured to advance the tube holder towards the mandrel; wherein the tube comprises PTFE, PVDF, a fluoropolymer, polyethylene, polypropylene, nylon, nylon copolymers, Pebax, polyacetal, or polyimide; where the shaped tube is a sheath having cylindrical portions of different diameter and made from a unitary piece of tubing, and a sloped or frusto-conical portion disposed between the cylindrical portions.

(30) A method, comprising: providing a hollow tube having a length; heating a mandrel, the mandrel having a first and second diameter portions; pushing the tube onto the mandrel so that the tube extends over both the first and second diameter portions, whereupon the mandrel increases the tube diameter over at least 10-20% of the tube length.

(31) The system of (28), method of (30), apparatus of (32), (33) or (34), in combination with one of, more than one of, or any combination in any order of the following list of things: further including the step of collect an image of the mandrel and tube before the tube extends over both the first and second diameter portions to determine whether the tube is oriented in a first direction relative to the mandrel; further including mounting the tube in a tube holder, the tube holder being coupled to a motor and using the motor to push the tube onto the mandrel; wherein the hollow tube is a first tube, further including placing a second tube within the first tube; further including shaping at least one end of the second tube after the second tube is within the first tube; and/or further including placing the tube over a medical device having a length, wherein the tube diameter increased by the mandrel extends over at least the length of the medical device, and wherein the medical device is a scaffold crimped to a balloon of a balloon catheter.

(32) An apparatus comprising: a catheter having a balloon; a medical device having a length and crimped to the balloon; and a sheath formed from a single piece of tubing, the sheath including: a constraining portion having a first diameter and applying a constraining force on the medical device, and a removing portion having a second diameter, greater than the first diameter, wherein lengths of both the constraining and removing portions are at least equal to or greater than the medical device length.

(33) An apparatus, comprising: a first sheath having a length; a second sheath having a length; and a catheter including a medical device crimped to a balloon, the catheter having a distal end and the medical device having a length; wherein the first and second sheaths are disposed over the medical device and have lengths that are greater than the length of the medical device; wherein the apparatus is configured for being implanted within a living body only if at least the second sheath is pulled off the distal end of the catheter such that the second sheath is removed by grasping the second sheath and pulling the second sheath across the medical device to thereby remove the second sheath from the catheter distal end.

(34) An apparatus, comprising: a tube; and a mandrel for shaping the tube when the mandrel is heated; a heating nozzle disposed in operative proximity to the mandrel and including an upper and lower housing separated by an opening including a heating space, wherein the opening permit entry of the mandrel and tube into the heating space in a first direction and removal of the mandrel and tube from the heating space in a second direction different from the first direction. The second direction may be perpendicular to the first direction.

INCORPORATION BY REFERENCE

All publications and patent applications cited and discussed in the present specification are herein incorporated by reference in their entirety, to the same extent as if each individual publication or patent application was specifically and individually indicated to be incorporated by reference in its entirety, including all figures, herein. To the extent there is an inconsistent usage of a word and/or phrase between an incorporated publication or patent application and the present specification, this word and/or phrase will have a meaning consistent with only the manner that the word and/or phrase is used in the present specification.

BRIEF DESCRIPTION OF THE DRAWINGS

FIG. 1B is a partial side view of the apparatus of FIG. 1A.

FIG. 5 shows a perspective view of a mandrel in accordance with the disclosure.

FIG. 5A shows a side-sectional view of the mandrel of FIG. 5 with a sheath disposed over the mandrel.

DETAILED DESCRIPTION OF EMBODIMENTS

Figure 1A:
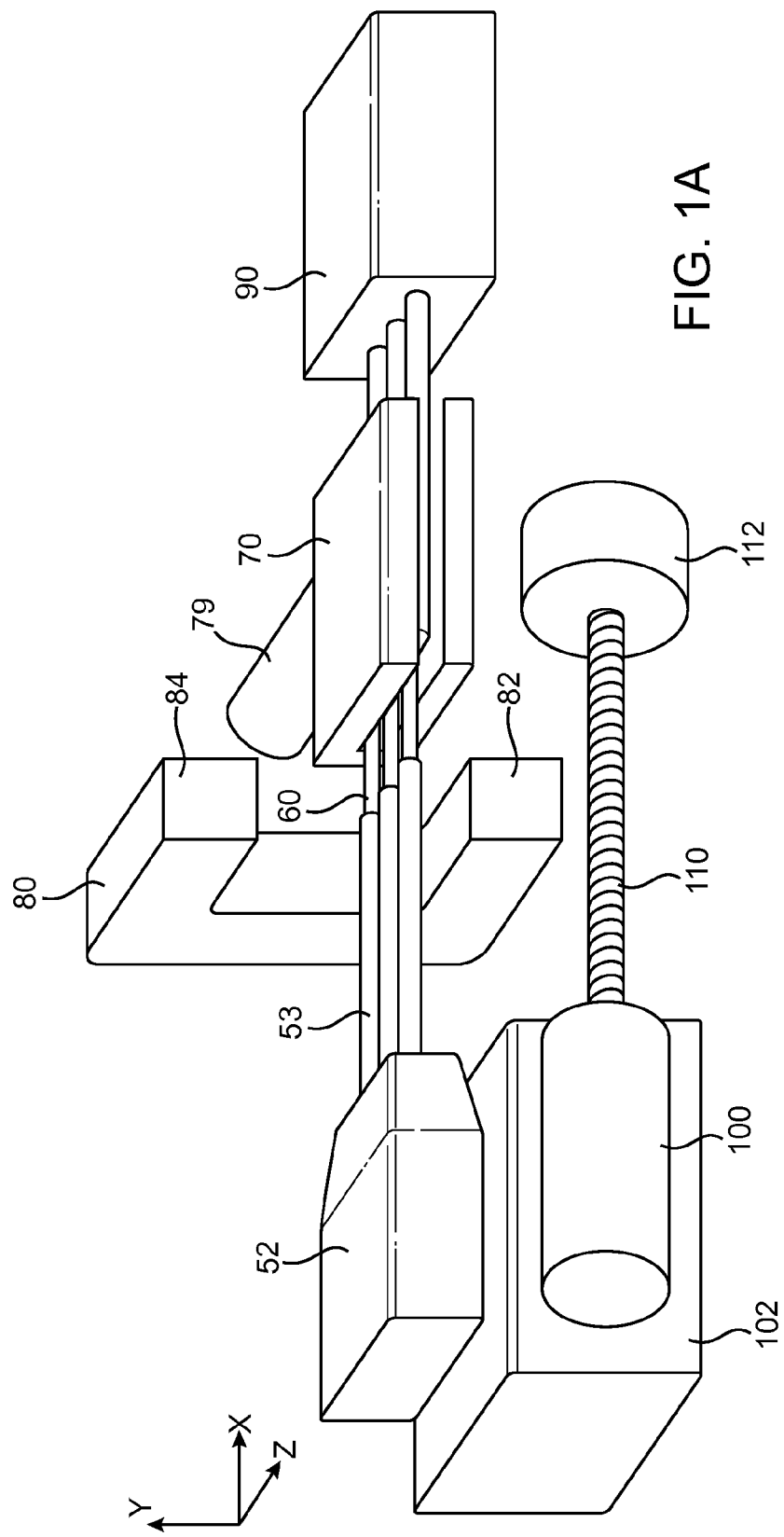
FIG. 1A is perspective view of an apparatus for making a sheath according to the disclosure.

For purposes of this disclosure, the following terms and definitions apply:

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, or between 1-2%, 1-3%, 1-5%, or 0.5%-5% different from d2. If d1 is a mean value, then d2 is about d1 means d2 is within a one-sigma, two-sigma, or three-sigma variation from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

U.S. application Ser. No. 13/924,421 filed Jun. 21, 2013 (the '421 application) includes a discussion about the meaning of terms such as "rigid," "Inflated diameter" or "expanded diameter," "post-dilation diameter," "pre-crimp diameter," "final crimped diameter," "recoil," "acute recoil," "radial," "circumferential," "axial" and "longitudinal."

A "crimping" of a stent or scaffold means, unless otherwise stated, a significant plastic or inelastic deformation of the stent or scaffold (body), such that when a radial restraint is removed from the crimped body, e.g., a constraining sheath is withdrawn, the scaffold or stent will change diameter (due to elastic recoil) by no more than about 5%, 10%, 20%, 30% or 50% increase from the crimped diameter. A body crimped to the balloon is held to the balloon by a retention force. A crimped body is deployed within the body by a balloon that imposes a significant inelastic or plastic deformation to expand the body to a deployed expanded or post-dilation diameter. The crimped body when deployed also has elastic recoil causing it to reduce in diameter by about 1, 2, 1-5%, 5-10% or 10%.

A structure X "configured for being implanted within a living body" means X is placed within a living body in use or X is capable of being placed within the body, e.g., delivered intraluminally through the vasculature of a living body. A structure Y not suited, capable or configured for being placed within a living body means if placed within the living body in a proscribed manner would pose serious health risks to the living body. A structure Z "configured for implantation only after . . . " means Z is placed within a living body in use or X is capable of being placed within the living body and delivered intraluminally through the vasculature of a living body only after a specific step is undertaken to convert Z to X. Thus, for example, an apparatus comprising a catheter, a scaffold mounted on a balloon and a two-piece sheath on the scaffold "configured for implantation in a living body only after . . . " the two-piece sheath is pulled distally to remove it from the scaffold (Z) means (Z) is converted to X only after "the two-piece sheath is pulled distally to remove it from the scaffold." In this example, a tearing, ripping or destruction of the sheath when removing it does not convert Z to X because the sheath was not pulled distally of the catheter to remove it from the catheter. Moreover, it will be understood, referring to preferred embodiments as examples, that when a two-piece sheath according to the disclosure is positioned over a scaffold there is no way available for the sheaths to be removed using the catheter proximal end handle. As such, it will be readily appreciated the meaning of "configured for implantation in a living body only after the sheath is removed" as there is no way other than sheath removal to configure the medical device for being implanted within a body.

Figure 7A:
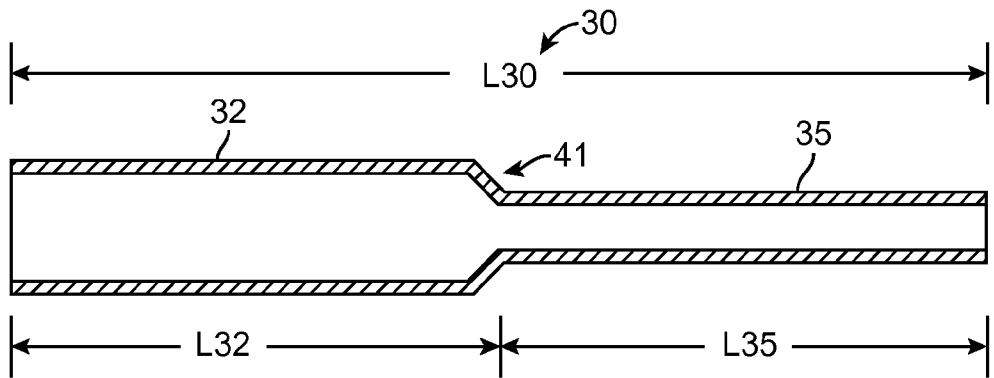
FIG. 7A is a side cross-sectional view of a constraining sheath made in accordance with the disclosure.

Referring to FIG. 7A, shown is a sheath 30 used to constrain or protect a polymer scaffold. The sheath 30 includes a first portion 35 having a first diameter, second portion 32 having a second diameter greater than the first diameter, and third portion 41 joining the portions 35, 32. Lengths L30, L32, L35 correspond to the total length of sheath 30, and the length of portions 32 and 35, respectively. The length L30 is equal to L35+L32 (portion 41 is included in the length L32). In a preferred embodiment 41 is a transition portion from the one to the other diameter portions 32, 35. The structure 41 describes a stepped section of the sheath 30 or step-down portion of the sheath 30 resulting from a manufacture process now described with reference to the following examples. The sheath 30 is made from a polymer, unitary tube of constant diameter (i.e., a cylinder). The cylinder is formed into the sheath 30 shown in FIG. 7A and having the portions 32, 35, 41. Examples of polymers that may be used to construct sheath 30 include Pebax, PTFE, polyethylene, polycarbonate, polyimide and nylon.

FIGS. 1A and 1B show aspects of a preferred apparatus 50 for fabricating the sheath 30. The apparatus 50 generally includes a tube handling portion 50a and a sheath forming portion 50b. The holding portion 50a holds tubes 53 received within suitable slots (not shown) of a tube holder 52 and carriage, rail or mechanism (100, 110, 112) for moving the holder 52 in the X direction (FIG. 1A shows a rectangular X-Y-Z reference system). The sheath forming portion 50b includes a heating nozzle 70 and mandrels 60, which have a narrow portion and wide portion located proximal and distal, respectively, of the tubes 53 in FIG. 1A. The wide portion is used to expand the respective tubes 53 over a desired length of the tube 53, thereby forming the sheath 30. The mandrels 60 are heated by the nozzle 70 to raise tube 53 material above a glass transition temperature so that the material can be easily radially expanded as the tube 53 is pushed over the wide portion of the mandrels 60.

The tube holder 52 and tubes 53 are advanced in the X-direction to push the tubes 53 over the mandrels 60. The tube holder 52 is mounted on a rail and coupled to a stepper motor 100. The stepper motor 100 is coupled to a worm gear 110 (supported on its far end by a support 112) for pulling the tube holder 52 and tubes 53 over the gear 110 and towards the nozzle 70, thereby advancing the tubes 53 over the mandrels 60 and into a heating space of the nozzle 70. The mandrels 60 are supported by a holder 90 which may include a mechanism having a movable collar (not shown). The collar ejects the finished sheaths 30 from the mandrels 60 by pushing the sheaths 30 in −X direction off the mandrels 60.

A detection system 80 including a light emitter 84 and light detector 82 portion is used to verify that the tubes 53 are properly loaded on tips of the mandrels 60 before the process begins. If the tubes 53 are not properly loaded a control prevents the tube holder 52 from being advanced forward by the stepper motor 100.

With the tubes 53 properly loaded, everything (but the nozzle 70) is moved in the −Z direction towards the nozzle 70 to place the mandrels 60 within the heat space of the nozzle 70. Thus, FIG. 1A is showing the arrangement of the apparatus 50 after everything has been moved, since the mandrels 60 are within the nozzle 70. After the mandrels 60 have reached a steady state temperature within the nozzle 70 the stepper motor 100 advances the tube holder 52 towards the nozzle 70. The tubes 53 are pushed over the wide portion of the mandrels 60 to cause the tubes 53 to reform into the sheaths 30. Once the sheaths 30 are formed, the sheaths 30 and mandrels 60 remain in the nozzle 70 for a heat set.

The mandrel holder 90 is activated to remove the mandrels 60 with sheaths 30 thereupon from the heating space of the nozzle 70, i.e., by moving everything away from the nozzle 70 (+Z direction). The sheaths 30 and mandrels 60 are then allowed to cool. Forced air is directed towards the sheaths 30 and cool gas passed through the lumen of the mandrels 60 to accelerate the cooling process. After the sheaths 30 have cooled the mandrel holder 90 is used to remove the sheaths 30 from the mandrels 60.

Figure 2:
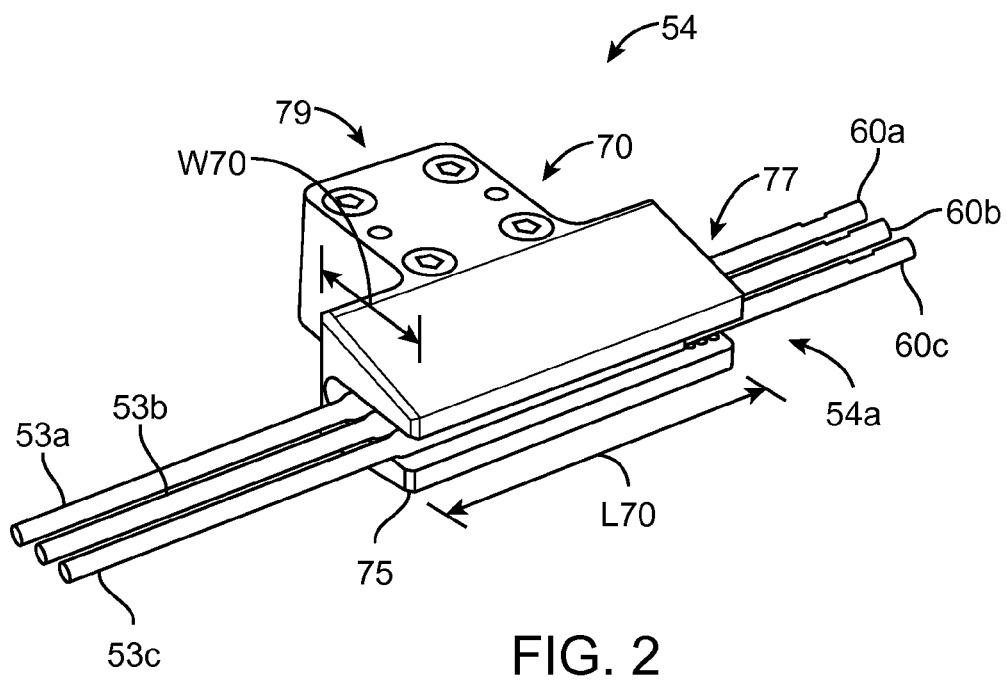
FIG. 2 is a perspective view of a nozzle, tubes and mandrels portions of the apparatus of FIG. 1A.

Referring to FIG. 2 there is shown the forming portion 54 including heat nozzle 70 and mandrels 60 according to a preferred embodiment. In this embodiment the forming portion 54 is configured to form three sheaths 30 simultaneously from three tubes 53a, 53b, 53c. As such, the heat nozzle 70 is sized to receive and heat at least three separate mandrels 60a, 60b, 60c for forming each of the respective at least three tubes 53a, 53b and 53c into sheaths 30.

Figure 2A:
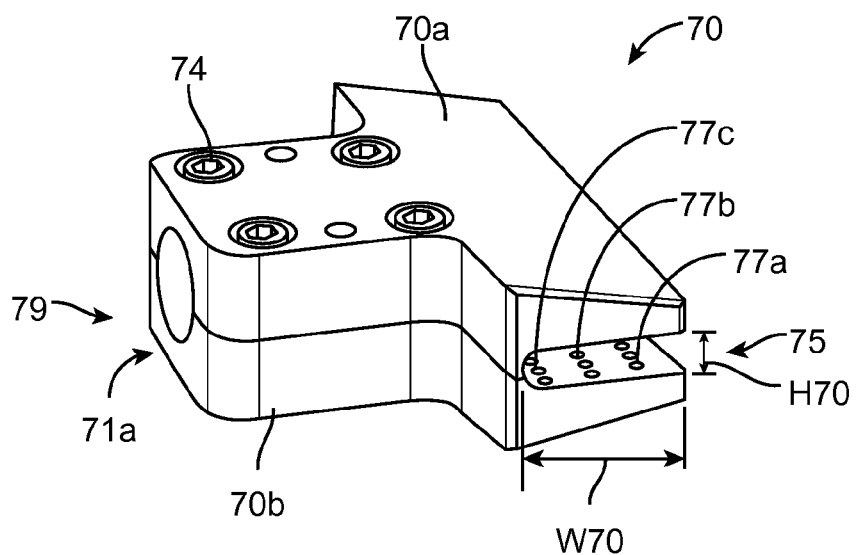
FIG. 2A is a perspective view of the nozzle of FIG. 2.
Figure 2B:
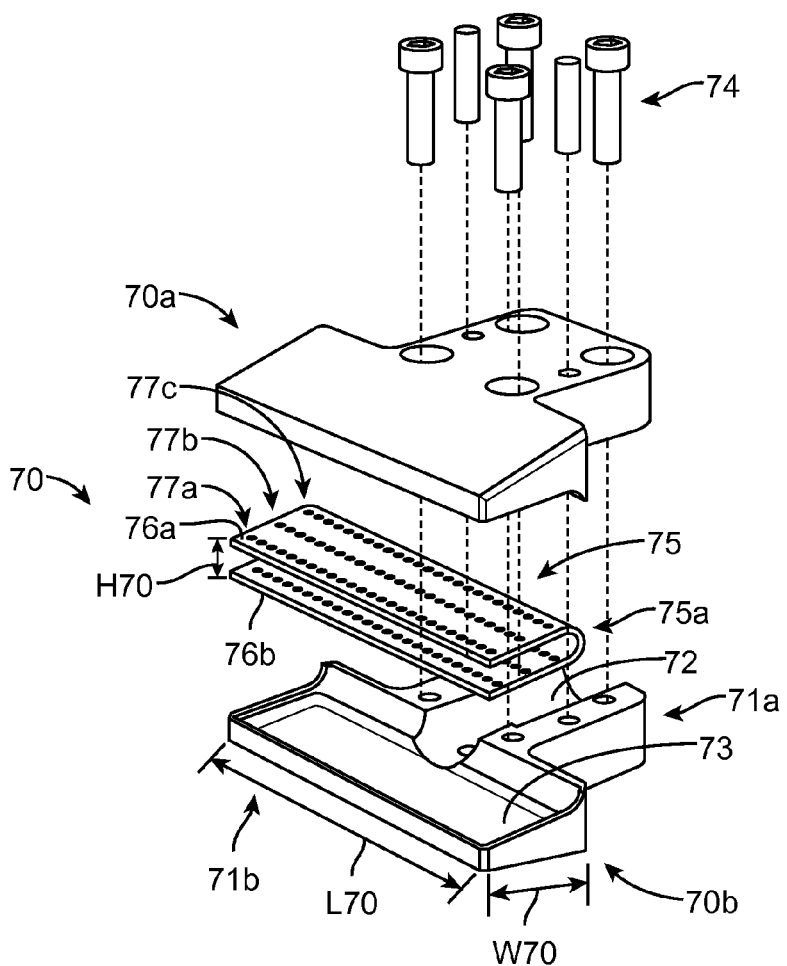
FIG. 2B is an exploded assembly view of the nozzle of FIG. 2A.
Figure 2C:
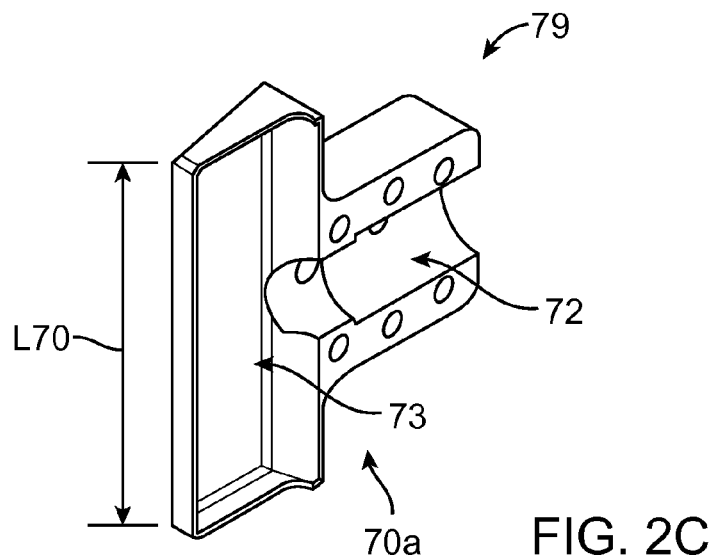
FIG. 2C is a perspective view of a housing portion for the nozzle of FIG. 2A.

The assembly and features of a preferred heat nozzle 70 are now described with reference to FIGS. 2A, 2B, 2C and 3. FIG. 2A shows an assembled view, FIG. 2B an exploded assembly view, FIG. 2C a portion 70a of the housing of the heat nozzle 70 and FIG. 3 an average temperature distribution over the heating space 54a verses the inflow temperature from heat source 79. The nozzle assembly includes an upper and lower housing 70a, 70b and heat distribution plate 75 secured together by fasteners 74. An upper housing 70b is the same as the lower housing in FIG. 2C for purposes of this description. Each housing half 70a, 70b forms a cavity 73 for accommodating the heat distribution plate 75 and gas flow into the heating space 54a, and one half of a round conduit 72 for passage of hot gas from the heat source 79 into towards the cavities 73. When assembled the housing cavities 73 form a partially open space and there is a round conduit and opening 71a for passage of the hot gas from the heat source 79.

The heat plate 75 is C-shape, having an upper part 76a, lower plate 76b and a curved end 75a connecting the parts 76a, 76b. Each plate 76a, 76b has arrays 77a, 77b, 77c of holes. The arrays of holes 77 on top (portion 76a) are aligned with the arrays of holes 77 on bottom (portion 76b). The heat plate 75 is sealed within the respective upper and lower cavities 73 such that the hot gas exits form only the arrays of holes 77.

Between the upper and lower plates 76a, 76b there is defined the heating space 54a. The height of the space 54a is H70, the length is L70 and the width is W70, as illustrated in the drawings. In general, the dimensions H70, W70, L70 are chosen according to the following criteria:

W70: chosen to accommodate the number of mandrels and tubes for simultaneous forming of sheath 30, e.g., three mandrels and tubes in the preferred embodiment.

H70: the inner surfaces of parts 76a, 76b are close to the mandrel wide portion 64 when disposed within the space 54a wide portion 64, yet provide sufficient clearance for the tube 53 to be forcibly slid over the mandrel wide portion 64 within the heating space 54.

L70: chosen according to the desired length of the flared or deformed tube portion. In the preferred embodiment L70 is at least, or about L32 (FIG. 7A). In some embodiments L70 is at least, or about the length of the longest length L32 desired for a stent or scaffold. According to these embodiments a nozzle 70 therefore is configured for making sheaths for a plurality of different-length stents or scaffolds.

Figure 3:
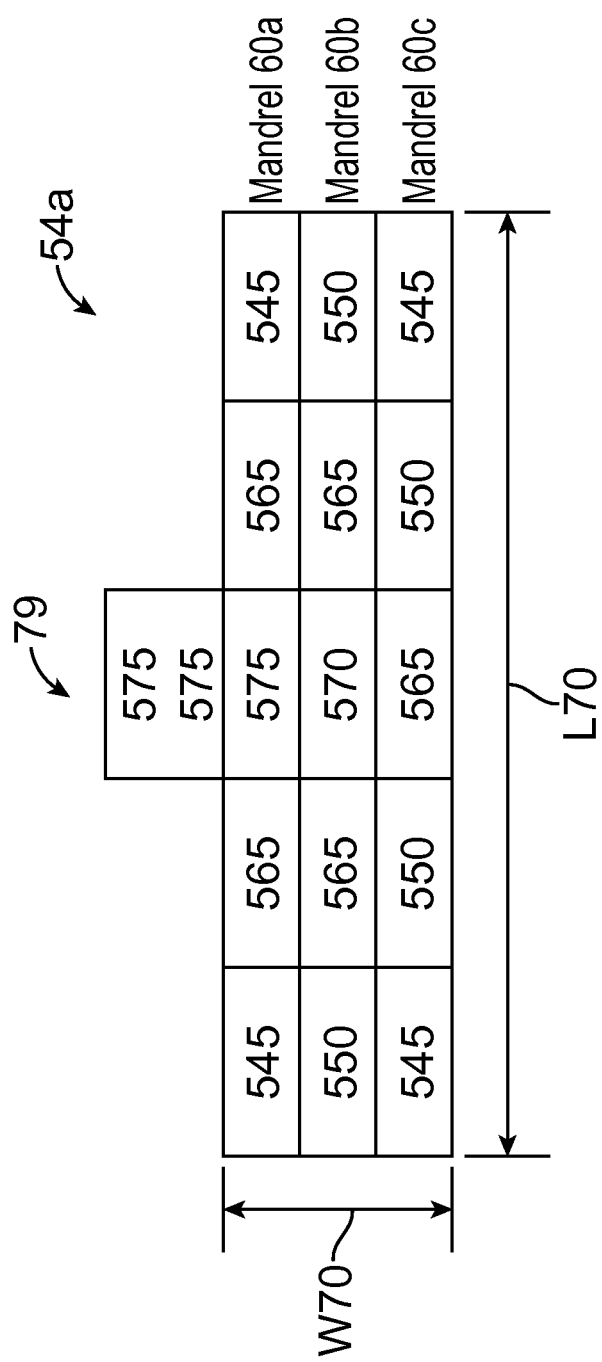
FIG. 3 shows a temperature distribution over a heating space for the nozzle of FIG. 2A.

The nozzle 70, in operation, is capable of maintaining a close to uniform temperature distribution throughout the heating space 54a. FIG. 3 illustrates the average temperature across the heating space. The incoming gas temperature is 575° F. As can be appreciated from FIG. 3 the variation in temperature across the heating space 54a is up to about 30° F. for the heating space 54a capable of heating up to three mandrels and simultaneously forming three sheaths 30. The inflow temperature is 575° F. The minimum temperature is 545° F.

Contributing to this outcome is the sizing and the number of the holes, and the inflow size (opening 71a receiving hot gas 79) as compared to the outflow size (i.e., total exit hole size on plate 75). Flow simulation was performed to arrive at an even heat distribution across all 3 mandrels 60a, 60b, 60c and over the length L70. Included in the calculations is an incoming flow cross section vs. outgoing flow cross section. In the preferred embodiment there are 150 (or 50 holes per mandrel) holes divided evenly into the arrays 77a, 77b, 77c across the top and bottom portions 76a, 76b of plate 75 and opposing each mandrel 60a, 60b, 60c. The sum total cross section of the holes 77 is less than the cross section of the inflow cross-section 71a. This difference in fluid input size verses exit size, which results in a positive pressure for space 54a at steady state flow, maintains hot air distribution over the expanding tubes 53 in spite of the nozzle openings and significant temperature gradient from inside the space 54a to ambient conditions near to the nozzle 70. The positive pressure limits the amount of heat conduction from the external environment to the interior of the heating space 54a, maintains the relatively even temperature within the heating space 54a and at the same time allows, by virtue of the three-sided opening, a processing of multiple parts in a single pass over the entire area (as opposed to the more time consuming task of localized heating that requires moving a mandrel and/or tube back and forth through a heat zone) and using a relatively simple sequence of few moving parts, e.g., as in FIG. 1A.

As indicated, the heating space 54a is open on three sides to allow the placement of the mandrels 60 and tubes 53 into the space 54a, and removal by lateral movement of the mandrel 60 and the sheath 30 thereupon. This feature of the nozzle 70 contributes to its usefulness during commercial production of many sheaths 30. By being able to maintain an even heat distribution, yet providing the open spaces on three sides (FIG. 2) for this movement into and out of the heating space 54a, greater efficiencies in a sheath manufacture process are realized.

In a preferred process, described in connection with the flowchart of FIG. 4, the tube 53 is passed over the mandrel 60 by the tube 53 passing through the opening defined by dimensions H70 and W70, which in the preferred embodiment receives up to three tubes over corresponding three mandrels at the same time. The mandrel 60 position in or out of the heating space 54a may be controlled by a mechanism (not shown) holding a proximal end 60b of the mandrel (FIGS. 5A, 5 discussed below). The opening opposite the opening where the tube 53 enters provides the space for displacing the mandrel 60 into and out of the heating space 54a. The opening defined by the dimensions L70 and H70 permits easy removal of the formed sheath 30 from the heating space 54a while still on the mandrel 60, as necessary to set the shape and allow cooling while on the mandrel 60.

Referring to FIGS. 5, 5A there is shown the mandrel 60 of the forming portion 50b used with the nozzle 70 (just described) to make a sheath 30. The mandrel 60 has a distal end 60a that receives the tube 53 on its tip 63, a proximal end 60b having a notch 61 secured to the holder 90, and the wide and narrow portions 64, 62 respectively. The wide portion 64 is placed within the heating space 54a and has an outer diameter corresponding to the inner diameter desired for the enlarged diameter portion 32 of the sheath 30 (FIG. 7A). The sheath 30 formed on the mandrel 60 is shown in FIG. 5A. The tube is pushed onto the mandrel wide portion 64 by the amount desired to form the length L32. This length may be at most the same as the length L70 of the heating space 54a. The mandrel 60 includes the narrow portion 62 (which has an outer diameter less than the outer diameter of the tube 53) to help support or prevent sagging or buckling of the tube 53 when it is being forcibly pushed over the wide portion 64 in the heating space 54a.

The mandrel 60 is made hollow having an internal bore 64. Coupled at the proximal end 60b is a heat sink source or passage to provide a cooling gas through the bore 64 to rapidly cool down the mandrel 60 after the sheath 30 is formed and mandrel 60 removed from the heating space 54a. The hollow mandrel provides distinct advantages over a solid mandrel—the mandrel can be heated and cooled much more rapidly than a solid mandrel, which improves production efficiencies. In the preferred embodiment the mandrel 60 has the following characteristics (TABLE 1). The mandrel 60 is made from stainless steel or equivalent material.

TABLE 1

| Wide portion 64 (outer diameter) | narrow portion 62 (outer diameter) | Wall thickness | Overall length | L32 | Angle (transition from portion 62 to portion 64) |
|---|---|---|---|---|---|
| .115 in | .085 in | .008–.010 in | 4.7 in | 1.7 in | 15 degrees |

It will be understood from the foregoing that a mandrel having these properties can be easily broken if subjected to a transverse loading. For this reason a detection system may include monitoring of the tip 63 of the mandrel for lateral deflections. Thus, use of the hollow mandrel 60, with its advantages in facilitating more rapid heating and cooling times, comes at somewhat of a price. There is also the consideration that the mandrel 60 is fragile because it is hollow (as opposed to solid throughout). Thus, the mandrel 60 may be easily broken or damaged.

As mentioned earlier, the hollow mandrel allows for more rapid heating and cooling times. In the contemplated embodiments it is therefore desired to use an effectively thin-walled tube for forming the sheath. It will be understand that given the diameter of the tubes formed by the mandrel can be too fragile of the walls are made too thin. Taking this into consideration it is contemplated that a mandrel according to these objectives may have a maximum ratio of outer diameter to wall thickness of between about 15 and 5, or more preferably between 11 and 8.

Figure 4:
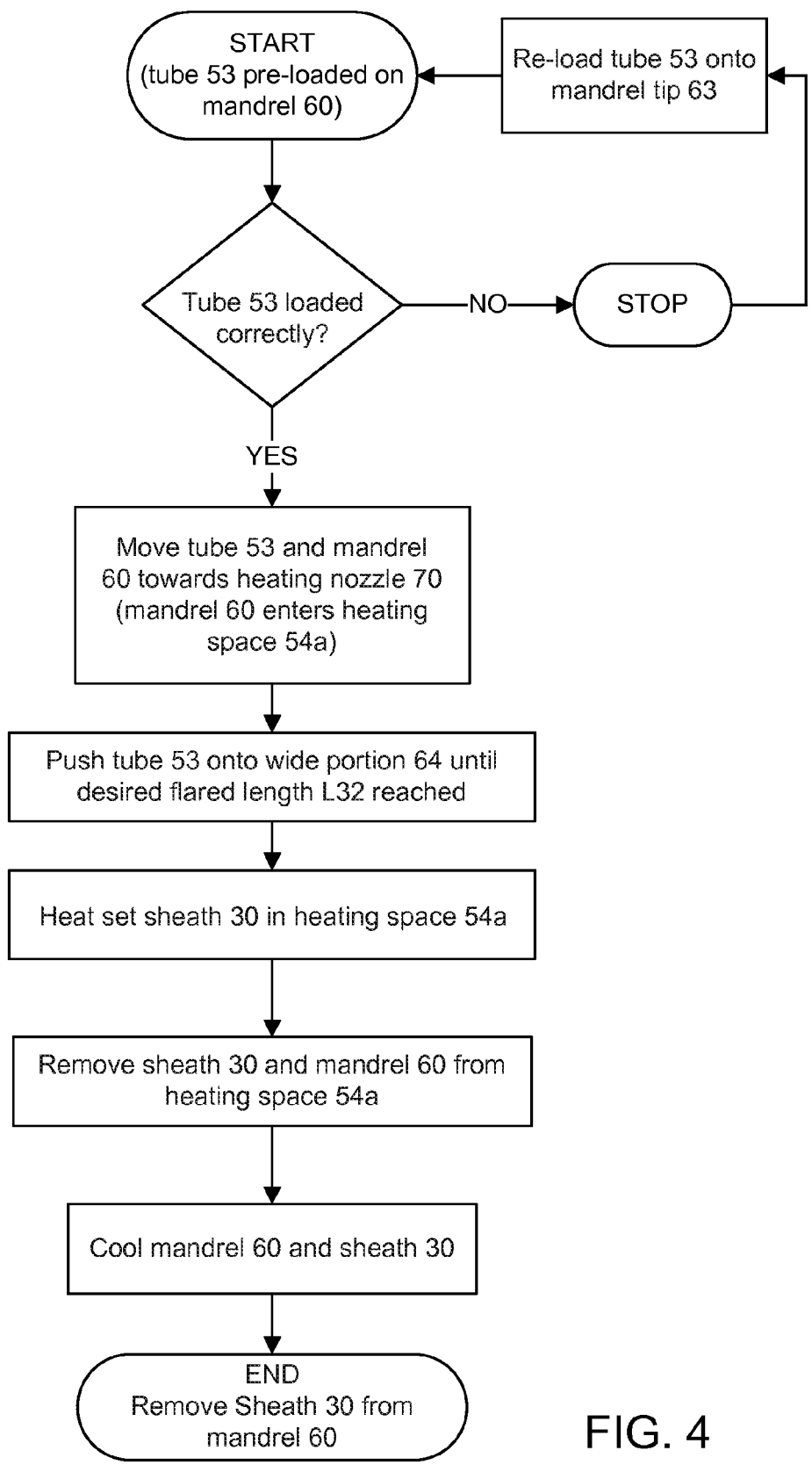
FIG. 4 shows a flow process for making a sheath in accordance with the disclosure.

FIG. 4 summarizes a flow process for forming the sheath 30 in accordance with the disclosure. The process is described in terms of a single tube that is made into the sheath 30. However, it is understood that the same steps can be carried out for two, three or more tubes simultaneously (three tubes in the preferred embodiment).

The process is preferably implemented as an automated process using the apparatus 50; so that movement of the tube 53 over the mandrel 60, and heating and cooling of the sheath 30 are performed under a computer control. The tube 53 is placed on the tip 63 of the mandrel 60. Before the tube 53 is advanced over the mandrel 60, a detection system located over the tube 53 and mandrel 60 verifies whether the tube 53 was loaded properly. The detection system may include one or more LEDs, CCD camera, or light emitter and an opposing photo-receptor, receiver or sensor (in the preferred embodiment shown in FIGS. 1A-1B the detector 80 is an area sensor and the portion 84 an emitter and 82 a receiver). When properly loaded the detection system detects a thickness or dimension of the tube 53 over the mandrel 70 corresponding to the appropriate dimensions for a properly loaded tube. When improperly loaded the detection system detects an improper dimension, such as a tube width adjacent a width of the narrow portion 62 of the mandrel 60. If an improper loading is detected, the process fails to initiate. The tube 53 must be re-loaded and the tube loading checked again before the process will initiate. In a preferred embodiment a detection system was implemented when tubes improperly loaded onto a hollow mandrel caused the mandrel 60 to break.

As mentioned above, in a preferred embodiment the detection system includes an area sensor, e.g., http://www.i-a.omron.com/products/family/1932/specification.html (downloaded Feb. 27, 2014), with amplifier. This sensor type produces one or more thin beams of light to detect movement or objects and operates in a similar manner as a bar code scan. The beam is picked up by a receiver and generates a varying analog output signal based upon the percent of the beam being block. During setup, the logic of the system records a value for the amount of blockage occurring when only the mandrels are present and a second value when the sheath blanks are installed over the mandrels. A range of approximately +\−20% is calculated to accommodate for variation in sheath blank dimensions. When the sensor has an output within this range the process begins and the blank (tube 53) is pushed towards the nozzle 70. Below this range indicates one or more blanks (tubes 53) are not installed over the mandrel(s) 60. Above this range indicates the sheath blanks are present but one or more are miss-aligned and not properly installed on the mandrels 60.

With the tube 53 properly loaded the mandrel 60 and tube 53 are moved towards the heating nozzle 70, which is coupled to a heat source, e.g., hot gas. The tube 53 is pushed onto the mandrel wide portion 64 and enters the heating space 54a. When the desired length L32 is reached, tube advancement ends. The tube 53 and mandrel 60 stay in the heating space 54a for a period of time to heat-set the formed sheath 30.

The tube 53 and mandrel 60 then exit from the nozzle 70 to allow for cooling within the sheath 30 while on the mandrel 60. In a preferred embodiment cool gas is passed through the lumen of the mandrel 60 and/or forced air is directed over the sheath 30 and mandrel 60 during this cooling process.

After the cooling step, a sleeve connected to a mandrel holder pushes the formed sheath 30 off of the mandrel 60.

The following description is directed to preferred embodiments of a polymer scaffold crimped to a balloon of a balloon catheter and protected by a protective sheath. The apparatus is configured for implantation within a living body only after the sheath is removed from the catheter. This sheath includes a constraining or outer sheath manufactured according to the above process.

A polymer scaffold is formed from a radially expanded or biaxially expanded extruded PLLA tube. The degree of radial expansion (RE) and axial expansion (AE) that the polymer tube undergoes can characterize the degree of induced circumferential molecular and crystal orientation as well as strength in a circumferential direction. In some embodiments the RE is about 400% and the AE is 40-50%. Other embodiments of processing parameters, RE and AE expansions considered within the scope of the disclosure are found in U.S. application Ser. No. 13/840,257 filed Mar. 15, 2013. The scaffold is laser cut from the expanded tube. The diameter of the tube is preferably selected to be about the same, or larger than the intended deployed diameter for the scaffold to provided desirable radial strength characteristics, as explained earlier. The scaffold is then crimped onto the balloon of the balloon catheter. Preferably, an iris-type crimping mechanism is used to crimp the scaffold to the balloon. The desired crimped profile for the scaffold is ½ or less than ½ of the starting (pre crimp) diameter of the expanded tube and scaffold. In the embodiments, the ratio of the starting diameter or pre-crimp diameter to the final crimp diameter may be 2:1, 2.5:1, 3:1, or higher and the pre-crimp diameter may be about 0.9 to about 1.5 higher than the balloon nominal inflation diameter. The ratio of pre-crimp or intermediate crimp diameter to final crimped diameter may be greater than a ratio of expanded or post-dilation diameter to the final crimped diameter of the scaffold.

The pre-crimp memory in the scaffold material following crimping will induce some recoil when the scaffold is removed from the crimper. While a dwell period within the crimper can reduce this recoil tendency, there is residual recoil to restrain while the scaffold awaits use. This is done by placing a restraining sheath over the scaffold after the crimper blades are released and the scaffold removed from the crimper head. This need to reduce recoil is particularly evident when the diameter reduction during crimping is high, e.g., as in above examples, since for a larger starting diameter compared to the crimped diameter the crimped material can have higher recoil tendencies. Examples of polymers that may be used to construct sheaths described herein are Pebax, PTFE, polyethylene, polycarbonate, polyimide and nylon. Examples of restraining sheaths for polymer scaffold, and methods for attaching and removing restraining sheaths for polymer scaffold are described in US20120109281, US20120324696 and U.S. Pat. No. 8,414, 528, and U.S. application Ser. No. 13/708,638.

Figure 6:
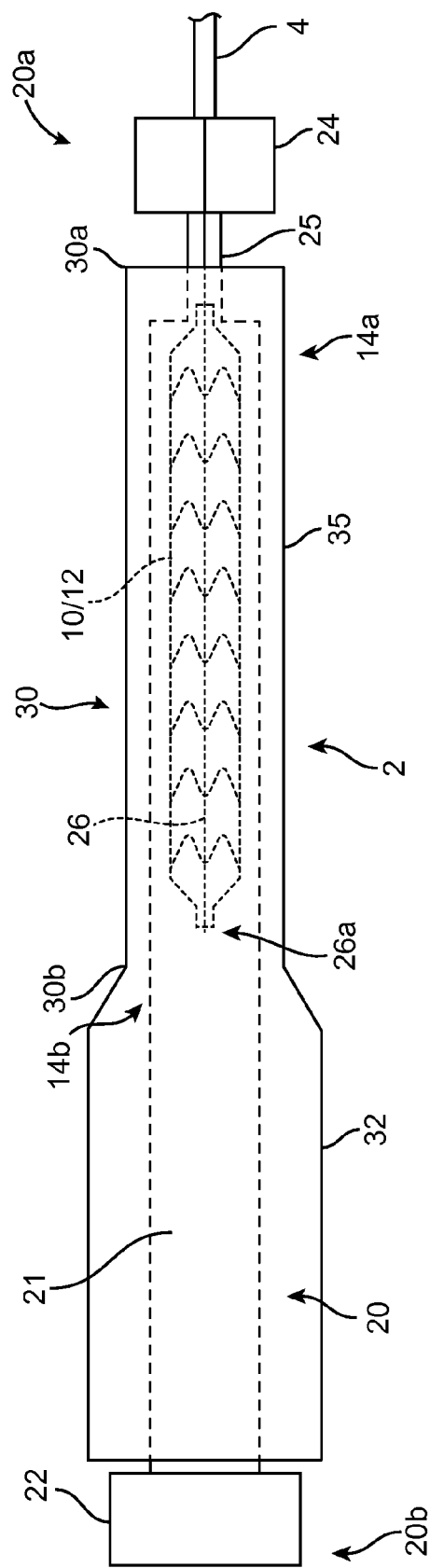
FIG. 6 is a side view of a medical device including a two-piece sheath according to the disclosure and placed over a scaffold and balloon of a balloon catheter.

FIG. 6 shows a side view of a distal portion of a scaffold-balloon catheter assembly 2. The catheter assembly 2 includes a catheter shaft 4 and a scaffold 10 crimped to a delivery balloon 12. As shown there are two separate sheaths 20, 30 disposed over the scaffold 10. The scaffold 10 is contained within a protecting sheath 20 and a constraining sheath 30, which is slid over the outer surface of the protecting sheath 20 to position it over the scaffold 10. Before inserting the catheter assembly 2 distal end within a patient, both the constraining sheath 30 and protecting sheath 20 are removed by a health professional.

The sheaths 20, 30 may be configured to provide an effective radial constraint for reducing recoil in the crimped scaffold 10, in addition to protecting the scaffold and balloon prior to use. The sheaths 20, 30 are removed by a health professional at the time of a medical procedure by pulling or pushing the outer sheath 30 towards the distal end of the scaffold 10 and balloon 12. With regard to other known devices, the removal of a single sheath covering a medical device can cause damage to the medical device. As described herein, a sheath that applies a radial constraint can be difficult to manually remove without adversely affecting the structural integrity of the medical device. In these cases, it is desirable to arrange the sheaths so that special handling is not required by the health professional when the sheath is manually removed. By making the sheath removal process easy to follow or intuitive, the possibility that a health professional will damage the medical device by improperly removing the sheath is reduced.

It is understood that if there are excessive pulling forces on the scaffold 10 when sheaths are removed, the catheter shaft 4 may be damaged, the scaffold 10 may dislodge from a balloon 12, or shift on the balloon 12; thereby reducing scaffold-balloon engagement relied on to hold the scaffold 10 to the balloon 12. Although imposing a tight fit on the scaffold 10 (through sheath 20), sheath 30, however, can be safely removed by a health professional without risk of damaging the medical device. Prior to sheath removal, it will be well understood that the device cannot be used since it cannot be placed within a living body.

When the scaffold 10 is constrained by sheath 30, as in FIG. 6, the constraining sheath 30 is located over the section of the protecting sheath 20 where the crimped scaffold 10 is found. This sheath 30 is made from a polymer tube material having a thickness and pre-stressed inner diameter size suitably chosen to cause the sheath 30 to apply a radially inward directed force on the scaffold 10. The thicker the tube and the smaller the pre-stressed inner diameter size for the sheath 30 the higher this constraint will be on the scaffold 10. If only sheath 30 were applied, i.e., the sheath 20 is not present, the amount of preload that the sheath 30 could apply to the scaffold 10 without affecting scaffold-balloon engagement would be limited. However, by introducing the protecting sheath 20 between the scaffold-balloon surface and sheath 30 the sheath 30 can impose a higher preload on the scaffold 10 without risk to the integrity of the scaffold-balloon engagement when the sheath 30 is applied to and/or removed from the scaffold 10. The protecting sheath 20 therefore serves to protect the integrity of the scaffold-balloon structure as the sheath 30 is repositioned relative to the scaffold 10. An example of a one-piece sheath capable of performing in a similar manner is found in US2012/0324696 at FIGS. 5 and 6A-6D. Other sheaths within the scope of the embodiments, including sheaths in combination with delivery tubes or coils, are found in U.S. application Ser. No. 13/924,421 filed Jun. 21, 2013.

The protecting sheath 20 extends over the entire length of the scaffold (as shown) and preferably beyond the distal tip of the catheter assembly 2 (as can be seen in FIG. 6) may the sheath 20 extend. The protecting sheath 20 is preferably formed from a unitary piece of polymer material, which is shaped to form differently sized portions 21, 22, 24 and 25 for protecting the scaffold/balloon 10/12.

At the distal end 20b of sheath 20 there is a raised end 22 in the form of a cylinder section having a larger diameter than the body portion 21 of the sheath 20 to the right of end 22 which covers the scaffold 10 in FIG. 6. Raised end 22 provides an abutting surface with respect to distal movement of sheath 30, i.e., neck 30b of sheath 30 abuts end 22 when sheath 30 is moved to the left in FIG. 6. End 22 and/or end 24 may alternatively take the shape of a frusto-conical or fluted end with the largest diameter end being furthest from portion 21. The raised end 22 may function to remove the sheaths 20, 30 simultaneously, as explained below.

Except as where noted herein, the protecting sheath 20 according to the disclosure may be the same, except as noted herein, as the protecting sheath described in US2012/0324696, US20120109281, US20120324696 and U.S. Pat. No. 8,414,528, and U.S. application Ser. No. 13/708,638.

Referring to FIGS. 6, 7B, 7C and 8B, the protecting sheath 20 has a cut 26, extending from the proximal end 20a to a location about at the distal the tip of the catheter assembly 2 (or sheath 20). The cut 26 forms an upper and lower separable halve 28, 29 of the sheath 20 (FIG. 8C). These halves 29, 28 are configured to freely move apart when the sheath 30 is positioned towards the distal end 20b. The location 26a may be thought of as a living hinge 26a about which the upper half 29 and lower half 28 of the sheath 20 can rotate, or deflect away from the scaffold 10. When sheath 30 is moved distally of the scaffold 10 in FIG. 6, the halves 28, 29 will tend to open up naturally, due to the preload applied by sheath 30 near hinge 26a. This arrangement for halves 29, 28 provides easy removal of sheath 20 from the scaffold 10, with minimal disruption to scaffold-balloon structural integrity, after sheath 30 is moved towards distal end 20b. When sheath 30 is fitted over the scaffold 10 or removed from the scaffold 10, the presence of the halves 28, 29 prevent direct contact between the sliding sheath 30 and the surface of the scaffold 10.

Figure 7B:
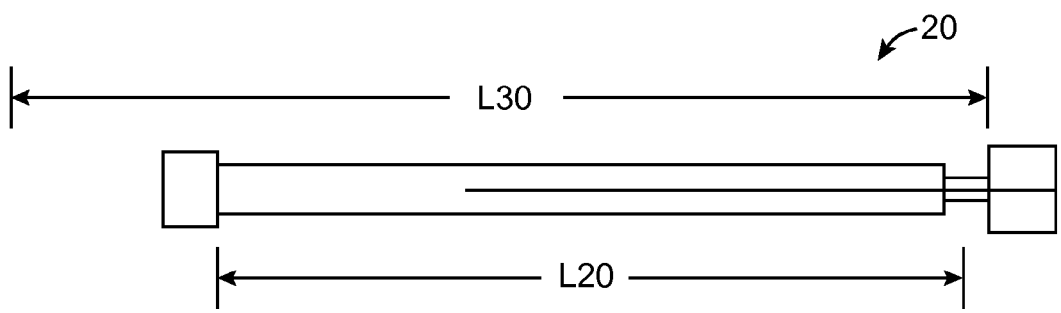
FIG. 7B is a side view of a protecting sheath made in accordance with the disclosure.

Sheath 20 may alternatively be formed as two completely separable halves, e.g., as halves 145a and 140a illustrated in FIG. 11C of US 2012/0324696 or as the same two halves shown in FIG. 7B but with the cut 26 running the length of, or substantially the entire length of the sheath 20. In the case of the former sheath 20 embodiment, sheath 150 of FIG. 11C of US2012/0324696 is replaced by the sheath 30 illustrated in FIG. 6 or other suitable embodiments thereof.

Embodiments of proximal end 20a of sheath 20 and methods of use are discussed in previously cited sheath disclosures, e.g., FIG. 1A and the accompanying discussion in U.S. Pat. No. 8,414,528. Referring to this disclosure and the foregoing, it is understood that scaffold-balloon integrity may be protected by the presence of the halves 28, 29 and the notched portion 25.

In some embodiments the sheath 20 may extend to about the end of the catheter and preferably at least to the end of the catheter. In a preferred embodiment an extended length of sheath 20, beyond the tip of the catheter assembly 2, e.g., may be about equal to a length of the scaffold 10 greater than this length. This length beyond the distal tip may facilitate an intuitive sliding removal or attachment of the sheath 30 from/to the scaffold 10 by respectively sliding the sheath 30 along the sheath 20 extension that is beyond the distal tip of the catheter assembly 2. Or this extended length allows the sheaths 20, 30 to be removed with the same pulling motion while the search 30 is not applying a radial constraint on the scaffold. The length of the sheath 20 that extends beyond the distal end of the catheter assembly 2 (length L21 in FIG. 4A of US2012/0324696) may depend on the choice of sheaths used. For example, from the perspective of the health professional removal process, if the sheath 20 is more stiff (e.g., higher wall thickness and/or modulus) relative to the sheath 30 then the length beyond distal end 4 for sheath 20 may be longer so that the halves 28, 29 of sheath 20 can be more safely displaced from the scaffold 10 by clearing the sheath 30 more distally of the scaffold 10. If the sheath 30 wall thickness and/or modulus is higher relative to sheath 20 than the length may be shorter since the sheath 30 will tend to naturally open up the halves 28, 29 as it is moved distally of the distal tip of the catheter assembly 2. Also, a thicker or higher modulus sheath 20 and/or sheath 30 may be desirable to increase the resistance to improper removal of sheath 20, e.g., as when a user attempts to remove sheath 20 with, or before removing sheath 30 from the scaffold 10 (as discussed earlier).

Referring to FIGS. 6, 6A-6C and 8A-8C the constraining sheath 30 includes a first portion 35 having a first diameter, second portion 32 having a second diameter greater than the first diameter, and third portion 41 joining the portions 35, 32. In the preferred embodiment 41 is a transition portion from the one to the other diameter portions 32, 35. The structure 41 is a sloped or step-down portion of the sheath 30 resulting from the manufacture process for the sheath 30 described earlier. As previously discussed, in the preferred embodiment a unitary tube of constant diameter throughout is made into the sheath 30 having the portions 32, 35, 41.

Methods of assembly of a medical device according to some aspects of the disclosure are now described. The medical device in its assembled state includes the scaffold crimped to a balloon catheter, the two piece sheath disposed over the scaffold as in FIG. 6, and the catheter being contained within a protecting tube. The catheter assembly 2 with sheaths arranged as in FIG. 6 may be contained within a protecting tube, hermetically sealed and sterilized. At the time when the catheter assembly is to be used in a medical procedure the package is opened and the tube and sheath pair is removed before implantation.

Before the sheaths 20/30 are placed, the scaffold 10 is crimped to the balloon 12 of the catheter assembly 2 using a crimping mechanism. As noted above, for a polymer scaffold the diameter reduction during crimping may be 2:1, 2.5:1, 3:1, 4:1 or higher. The scaffold may be placed on a balloon having a nominal, expanded or post-dilation diameter that is about 2, 2.5, or 3 times the diameter of the scaffold when the scaffold has a final crimp diameter on the balloon. The diameter reduction (from a pre-crimp size to the final crimp diameter) introduces high stresses in the scaffold structure. The memory in the material following crimping causes recoil of the scaffold structure, as discussed earlier; one can incorporate lengthy dwell times within the crimper, e.g., after the final crimp step, to allow stress-relaxation to occur in the structure while heated crimper blades are maintaining a fixed diameter and temperature to facilitate stress relaxation. Both the dwell period and the imposition of a constraining sheath over the crimped scaffold after crimping helps to reduce recoil after crimping. Crimping of the scaffold 10 to the balloon 12 including desirable dwell times and temperatures that can affect stress relaxation and recoil after crimping are disclosed in U.S. patent application Ser. No. 12/861,719, U.S. patent application Ser. No. 13/089,225 and U.S. patent application Ser. No. 13/107,666.

Following removal from a crimping mechanism the scaffold will recoil unless subject to a radial constraint. According to some aspects of the disclosure a temporary one-piece sheath is placed on the scaffold immediately following crimping, then replaced by the sheath of FIG. 6 after about ½ hour from removal from the crimping mechanism. Examples of the one-piece sheath according to the disclosure is one-piece sheath 23 described in U.S. application Ser. No. 13/708,638.

Figure 8A:
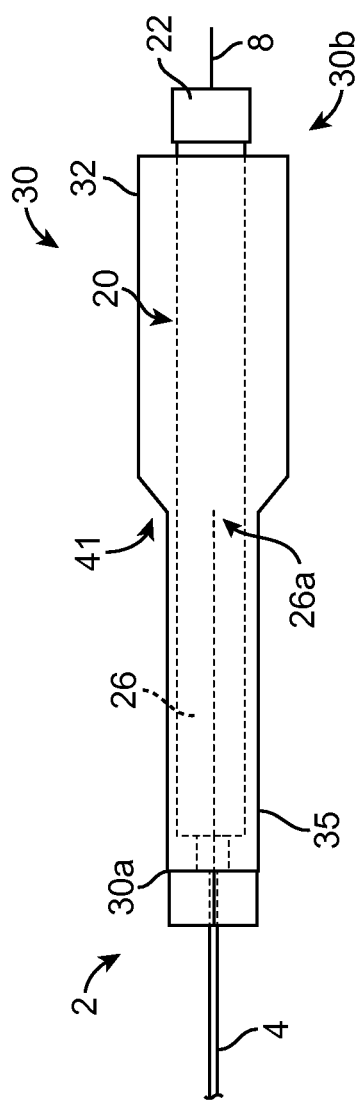
FIGS. 8A-8C illustrate steps for removing the sheaths of FIG. 7C from a catheter.
Figure 8B:
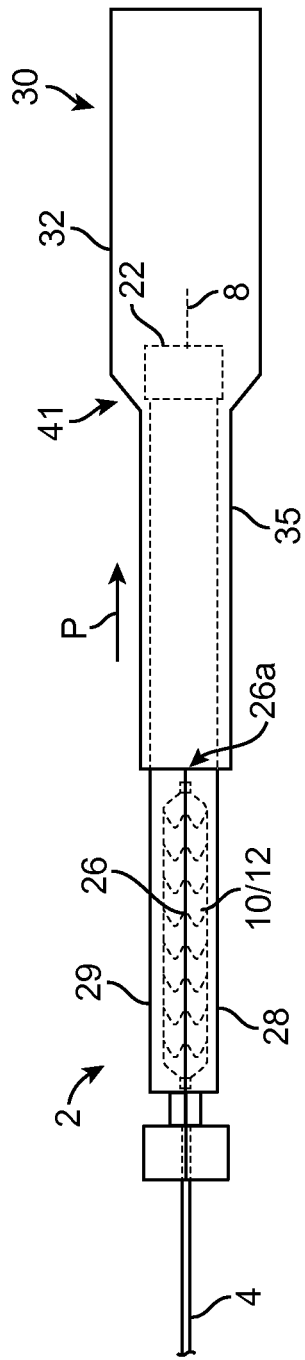
Figure 8C:
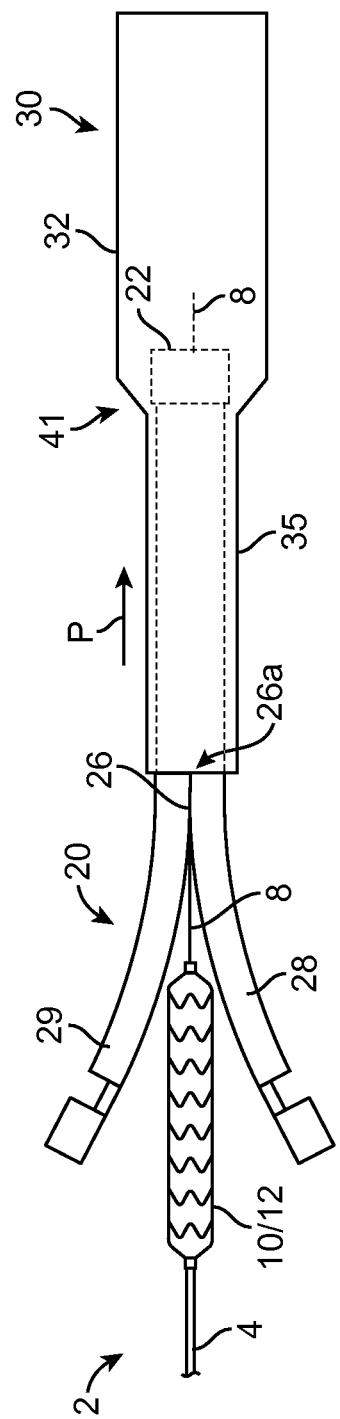

FIGS. 8A-8C illustrates a removal process for the sheath pair 20/30 by a medical professional. The assembly of the sheath pair 20/30 is described with reference to the same drawings. The sheath pair 20/30 may be attached as follows. The sheath pair may be placed on a mandrel 8 before the mandrel 8 is attached to the catheter assembly 2. The mandrel 8 is passed through the catheter shaft 4 guidewire lumen and exits at the distal end of the catheter assembly 2. The sheath pair is positioned distally of the catheter assembly 2. The mandrel 8 guides the sheath pair over the scaffold-balloon 10/12. The portion 41 is adjacent the raised end 22 of the sheath 20. In this configuration the halves 28, 29 can freely open or close. The sheath pair 20/30 may then be positioned over the scaffold-balloon 10/12 (as in FIG. 6) as follows. Holding the catheter assembly 2 stationary, grasping the mandrel 8 with one hand and the sheath pair with the other hand and sliding the sheath pair over the mandrel 8 until the halves 28, 29 are located over the scaffold-balloon 10/12 as shown in FIG. 8C. When properly positioned, the portions 24, 25 are positioned with respect to proximal end 14a as shown in FIG. 6.

Once the halves 28, 29 are located properly over the scaffold-balloon 10/12 to protect this structure, the constraining sheath 30 can be pushed over the scaffold-balloon 10/12. The sheath 30 may be pushed over the scaffold-balloon 10/12 in the following manner. The raised end 22 and mandrel 8 are grasped with one hand to hold the two stationary. Then, using the other hand the sheath 30 is pushed over the scaffold-balloon 10/12 until the end 30a of sheath 30 is disposed adjacent to, or abuts the raised end 24 of the sheath 20, which indicates the proximate location of the proximal end 14a (FIG. 6) of the balloon-scaffold 10/12. Alternatively, the portion 24 and catheter shaft 4 may be simultaneously held with on hand, while the sheath 30 is pushed towards the scaffold 10 with the other hand. By grasping the portion 24 with the catheter shaft 4, the halves 28, 29 are held in place relative to the scaffold 10 while the sheath 30 is being pushed over the scaffold 10.

With the sheath positioned over the scaffold as in FIG. 6, the catheter is placed within a tube or coil. The tube or coil, which may be rigid compared to the catheter shaft, protects the catheter during shipment/delivery and storage. When the packaged and sterile medical device is received by a health professional, it may be enclosed within a rigid tube to protect the contents inside from damage.

Figure 7C:
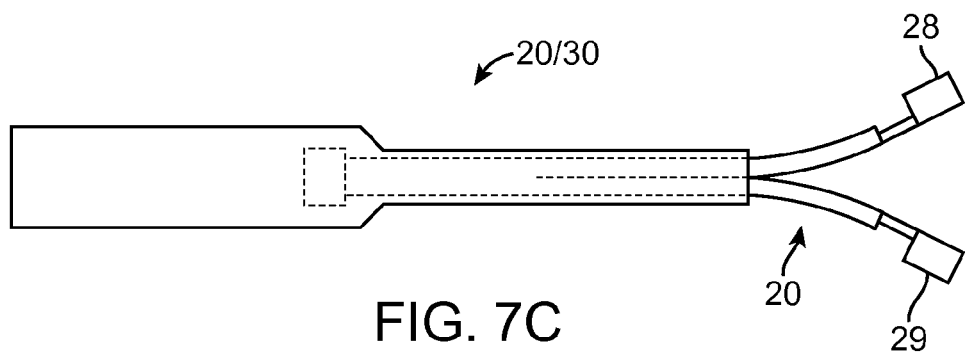
FIG. 7C is a side view showing an assembly of the sheaths in FIGS. 7A and 7B.

Referring to FIGS. 7A-7C there is shown lengths L30, L32, L35 and L20 which correspond to the total lengths of sheath 30, portions 32 and 35, and sheath 20. The length L30 is equal to L35+L32 (portion 41 is included in the length L32). The length L30 may be about or slightly less than L20. L20 may be longer than L30 by an amount about equal to the length of raised end 22. The inner diameter of portion L35 is less than the outer diameter of end 22 so that end 22 acts as a stop for sheath 30 when sheath 30 is pulled distally during removal from the catheter. L32 is greater than or about equal to the length of the balloon/scaffold 10/12.

The lengths L32 and/or L35 may be based on a length of a scaffold. For example, both L32 and L35 may be about or at least the length of a scaffold, so that the L30 is about twice the length of the scaffold. Scaffold lengths for coronary use may be about 12 mm, 18 mm, 20 mm or 30 mm. The lengths L32 and/or L35 may therefore be about or at least 12 mm, 18 mm, 20 mm or 30 mm or be about or at least 12-20 mm, or be about or at least 12-18 mm or be about or at least 20-30 mm. Scaffold lengths for peripheral use may be about 30 mm, 40 mm, 50 mm, 60 mm, 100 mm, or 200 mm. The lengths L32 and/or L35 may therefore be about or at least 30 mm, 40 mm, 50 mm, 60 mm, 100 mm, or 200 mm or be about or at least 30-60 mm, or be about or at least 100 to 200 mm or be about or at least 60-150 mm.

The portions 32 and 35 are both cylindrical, or have a constant diameter over their respective lengths, with the exception of the sloped 41. The sheath 30 in some embodiments has two cylindrical portions of different diameter and made from a unitary piece of tubing.

A method of removal of the sheath 20/30 from the scaffold 10 is now described. At the time when the catheter assembly is to be used in a medical procedure the package is opened and the sheath pair removed from the distal end. The catheter assembly 2 is not configured for being introduced into the patient until the sheath pair is removed. Referring again to FIG. 8A, there is depicted an arrangement of the sheaths 20, 30 at the distal end of the catheter assembly 2 when the packaged and sterile medical device is received by a health professional. Examples of such sterile packaging is found in U.S. patent publication no. US 2008-0010947.

The sheath 20 may extend well-beyond the distal end of the catheter 2 assembly. The end 22 may overhang or sit distal the catheter distal end by a full, half or ¼ the scaffold or length L30. The overhanging or distal portion with portion 32 substantially covering the distal portion (when received by the medical professional) helps to facilitate an intuitive removal of the sheath pair by a health professional, thereby reducing the chances that the sheath pair are removed improperly, such as a removal by pulling on, or gripping the sheath 20 instead of the portion 32.

Referring again to FIGS. 8A-8C, methods for removing the sheath pair from the scaffold-balloon 10/12 by the health professional are now described. These illustrations refer to moving the sheath pair over the mandrel 8; however, a mandrel 8 is not necessary. The sheath pair 30/20 may be safely removed from the catheter assembly 2 without using a mandrel 8.

A sterilized and packaged catheter assembly with sheaths 20, 30 positioned as shown in FIG. 8A typically includes the stiffening or storage mandrel 8 in the catheter shaft 4 lumen to provide bending stiffness for shaft 4. A distal end of the mandrel 8 has a curled end, or an extension/stop at the distal end (not shown), which is used to manually withdraw the mandrel 8 from the catheter shaft 4 lumen by pulling the mandrel 8 towards the distal end 6 of the catheter assembly 2. In the following example the sheaths 20, 30 are removed. The proscribed steps preferably also include the act of removing the mandrel 8 from the catheter shaft lumen by, e.g., simultaneously gripping the raised end 22, sheath 230 and mandrel 8.

First, the sheath 30 portion 32 is grabbed and pulled away from the scaffold-balloon 10/12 structure, which removes the constraining portion 35 from the scaffold-balloon 10/12 structure. The sheath 30 may be withdrawn or pulled away from the scaffold-balloon 10/12 in the following manner. One hand grasps the portion 30; the other hand grasps the catheter shaft 4 proximal of the scaffold 10 to hold the catheter 2 stationary. The sheath 30 is pulled in the direction P (FIG. 8B). When portion 41 abuts the stepped end 22 of sheath 20, the constraining portion 35 has cleared the scaffold. At this point continued pulling of the sheath 30 will also remove the sheath 20 from the scaffold and eventually separate the sheath 20/30 from the catheter 2. The raised end 22 therefore functions as an abutment for removing both sheaths in a safe manner with minimal disruption to the crimped scaffold.

According to a method of crimping, a crimping process at or near to a glass transition temperature of the polymer of the scaffold 10 is conducted as explained in U.S. application Ser. No. 13/644,347 including FIGS. 3A and 4A. Before placing a two-piece sheath as described above, a temporary sheath may be formed with slits or weakened areas that will facilitate a tearing away of the sheath when it is attached to the scaffold. Examples of such a sheath is described in U.S. application Ser. No. 13/708,638 as shown in FIGS. 2, 3A-3E and 4.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A method, comprising:
   using a heating space;
   using a mandrel having a small diameter section, a large diameter section and a sloped section separating the small and large diameter sections;
   using a hollow tube having a bore and solid walls surrounding the bore, wherein the tube is made from a polymer material, the tube has a length and forms a cylindrical portion having a first diameter, and the cylindrical portion extends over at least 25% of the tube length;
   holding the tube with a tube holder; and
   using the tube holder, pushing the tube over the mandrel to increase the first diameter of the cylindrical portion of the tube to a second diameter;
   wherein the large diameter section of the mandrel has the second diameter and a length of the large diameter section is greater than the at least 25% of the tube length; and
   wherein the large diameter section of the mandrel is disposed within the heating space and the small diameter section of the mandrel is disposed outside of the heating space when the tube is pushed over the mandrel.

2. The method of claim 1, wherein the mandrel is a hollow mandrel.

3. The method of claim 1, wherein the mandrel is heated to a steady state temperature using the heating space before the tube is pushed over the mandrel.

4. The method of claim 1, the method further including holding a plurality of the tubes with the tube holder and, using the tube holder, pushing each of the plurality of tubes over a corresponding one of a plurality of the mandrels to thereby form a plurality of shaped tubes each having its cylindrical portion first diameter increased to a second diameter.

5. The method of claim 1, wherein the tube length is between 20 and 200 mm.

6. The method of claim 1, wherein the tube holder is coupled to a motor configured to advance the tube holder towards the mandrel.

7. The method of claim 1, wherein the tube comprises PTFE, PVDF, a fluoropolymer, polyethylene, polypropylene, nylon, nylon copolymers, polyether block amide, polyacetal, or polyimide.

8. The method of claim 1, wherein the tube having the second diameter is a sheath adapted for being placed over a distal end of a balloon catheter.

9. A method, comprising:
using a heating nozzle, the nozzle comprising a first housing, a second housing and an opening including a heating space between the housings;
using a mandrel having a small diameter section, a large diameter section and a sloped section separating the small and large diameter sections;
using a hollow tube having a bore and solid walls surrounding the bore, wherein the tube is made from a polymer material, the tube has a length and forms a cylindrical portion having a first diameter, and the cylindrical portion extends over at least 25% of the tube length;
holding the tube with a tube holder; and
using the tube holder, pushing the tube over the mandrel to increase the first diameter of the cylindrical portion of the tube to a second diameter;
wherein the nozzle opening permits passage of the mandrel into the heating space in a first direction and removal of the mandrel from the heating space in a second direction that is about perpendicular to the first direction.

10. The method of claim 9, wherein the heating space is connected to a heat source supplying a gas having a temperature of at least 500 Deg. F.

11. The method of claim 10, wherein the temperature throughout the heating space varies by 1-5% from the supply gas temperature.

12. The method of claim 10, wherein the temperature throughout the heating space varies by less than 1% from the supply gas temperature.

13. The method of claim 9, wherein the tube having the second diameter is a sheath adapted for being placed over a distal end of a balloon catheter.

14. A method, comprising:
using a first, hollow tube having a bore and solid walls surrounding the bore, a length and a diameter, wherein the first tube is made from a polymer material;
heating a mandrel, the mandrel having first and second diameter portions;
while the mandrel is being heated, pushing the first tube onto the mandrel so that the first tube extends over both the first and second diameter portions of the mandrel, whereupon the mandrel increases the first tube diameter over at least 10-20% of the first tube length; and
after increasing the first tube diameter, placing a second tube within the first tube.

15. The method of claim 14, further including the step of collecting an image of the mandrel and first tube before the first tube extends over the first and second diameter portions, wherein the collected image indicates whether the first tube is oriented in a first direction relative to the mandrel.

16. The method of claim 14, further including mounting the first tube in a tube holder, the tube holder being coupled to a motor, and using the motor to push the first tube onto the mandrel.

17. The method of claim 14, further including shaping at least one end of the second tube after the second tube is placed within the first tube.

18. The method of claim 14, wherein the first tube and second tube form a two-piece sheath assembly adapted for being placed over a distal end of a balloon catheter, wherein the distal end is configured for being implanted into a body only after the two-piece sheath assembly is removed from the distal end.

19. A method, comprising:
shaping a hollow tube having a bore and solid walls surrounding the bore, a length and a diameter, wherein the tube is made from a polymer material, the shaping comprising:
heating a mandrel, the mandrel having a first diameter portion and a second diameter portion; and
pushing the tube onto the mandrel so that the tube extends over both the first and second diameter portions, whereupon the first diameter portion of the mandrel increases the tube diameter over at least 10-20% of the tube length; and
after shaping tube, placing the tube over a medical device having a length, wherein the at least 10-20% of the tube length is equal to, or greater than a length of the medical device, and
wherein the medical device is a scaffold crimped to a balloon of a balloon catheter.

* * * * *